US008136888B2

(12) United States Patent
Suzuki et al.

(10) Patent No.: US 8,136,888 B2
(45) Date of Patent: Mar. 20, 2012

(54) LIFTING METHOD FOR LESION AREA, AND ANCHORING DEVICE

(75) Inventors: Takayuki Suzuki, Yokohama (JP); Takeshi Ohdaira, Fukuoka (JP)

(73) Assignee: Olympus Medical Systems Corp., Tokyo (JP)

( * ) Notice: Subject to any disclaimer, the term of this patent is extended or adjusted under 35 U.S.C. 154(b) by 486 days.

(21) Appl. No.: 11/300,173

(22) Filed: Dec. 14, 2005

(65) Prior Publication Data
US 2007/0135678 A1  Jun. 14, 2007

(51) Int. Cl.
*A61M 37/00* (2006.01)
*A61N 2/00* (2006.01)
*A61F 2/00* (2006.01)
*A61F 13/00* (2006.01)
*A61B 10/00* (2006.01)

(52) U.S. Cl. .............................. 300/12; 600/37; 600/562
(58) Field of Classification Search .................... 600/37, 600/562, 12; 128/899, 898
See application file for complete search history.

(56) References Cited

U.S. PATENT DOCUMENTS

| 6,123,665 | A | * | 9/2000 | Kawano | 600/104 |
| 6,814,742 | B2 | * | 11/2004 | Kimura et al. | 606/151 |
| 7,014,646 | B2 | * | 3/2006 | Adams | 606/159 |
| 7,766,810 | B2 | * | 8/2010 | Ohdaira | 600/12 |
| 2002/0173805 | A1 | | 11/2002 | Matsuno | |
| 2004/0050395 | A1 | | 3/2004 | Ueda et al. | |
| 2004/0138682 | A1 | * | 7/2004 | Onuki et al. | 606/144 |
| 2004/0225305 | A1 | * | 11/2004 | Ewers et al. | 606/153 |
| 2005/0070763 | A1 | * | 3/2005 | Nobis et al. | 600/114 |
| 2005/0165272 | A1 | * | 7/2005 | Okada et al. | 600/114 |

FOREIGN PATENT DOCUMENTS

| JP | 08-256973 | 10/1996 |
| JP | 2002-159508 | 6/2002 |
| JP | 2004-105247 | 4/2004 |
| JP | 2004-321692 | 11/2004 |
| JP | 2004-357816 | 12/2004 |

OTHER PUBLICATIONS

U.S. Appl. No. 11/076,662, filed Oct. 3, 2005, Ohdaira.
"4.3.6 Hard and Soft Magnets", dated Nov. 9, 2005. http://www.techfak.uni-kiel.de/matwis/amat/elmat_en/kap_4/backbone/r4_3_6.html.

* cited by examiner

*Primary Examiner* — Max Hindenburg
*Assistant Examiner* — Adam Eiseman
(74) *Attorney, Agent, or Firm* — Scully, Scott, Murphy & Presser, P.C.

(57) ABSTRACT

A lifting method for a lesion area of the present invention includes: a step of introducing an anchoring tool having a magnetic body and an anchor into a hollow organ having a lesion area, by using a working channel inserted from a natural opening into the hollow organ; a step of anchoring the anchoring tool, by sequentially placing the anchor in a predetermined position around the lesion area, so as to arrange a plurality of the magnetic bodies around the lesion area; and a step of lifting a tissue including the lesion area, by attracting the magnetic bodies using the magnetic field generation tool arranged on the outside of the hollow organ.

10 Claims, 29 Drawing Sheets

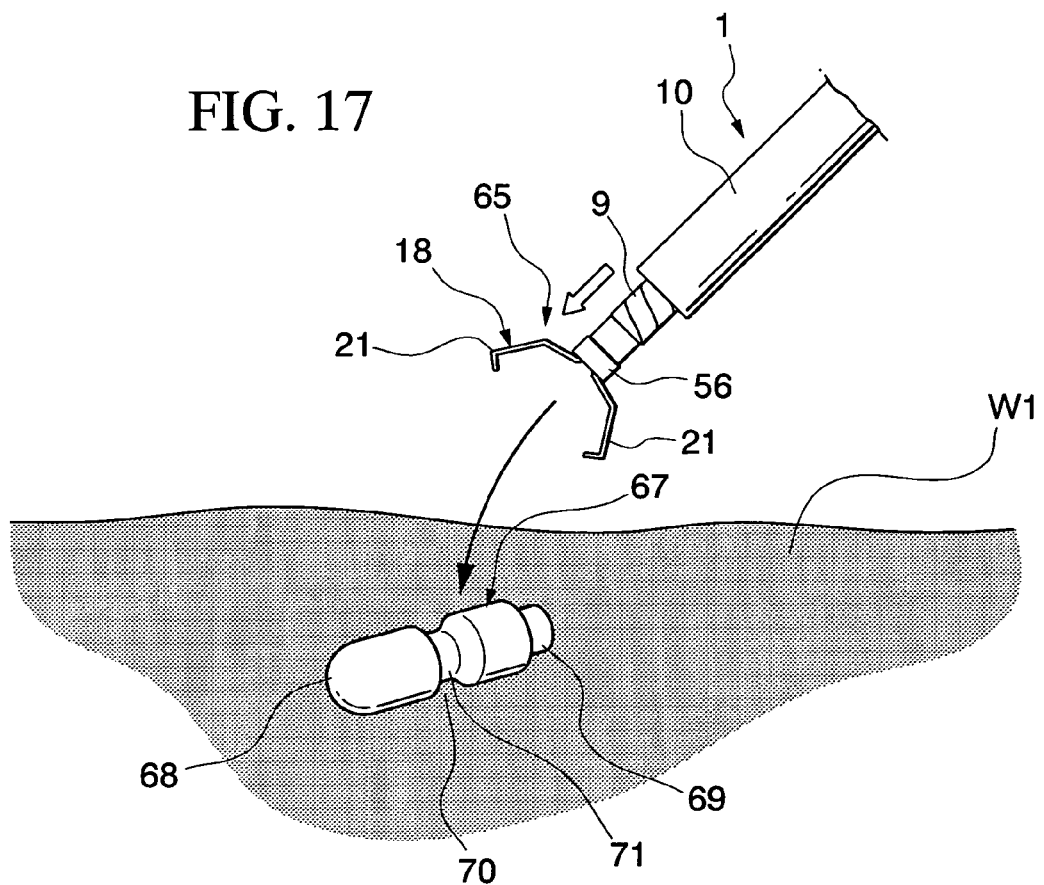
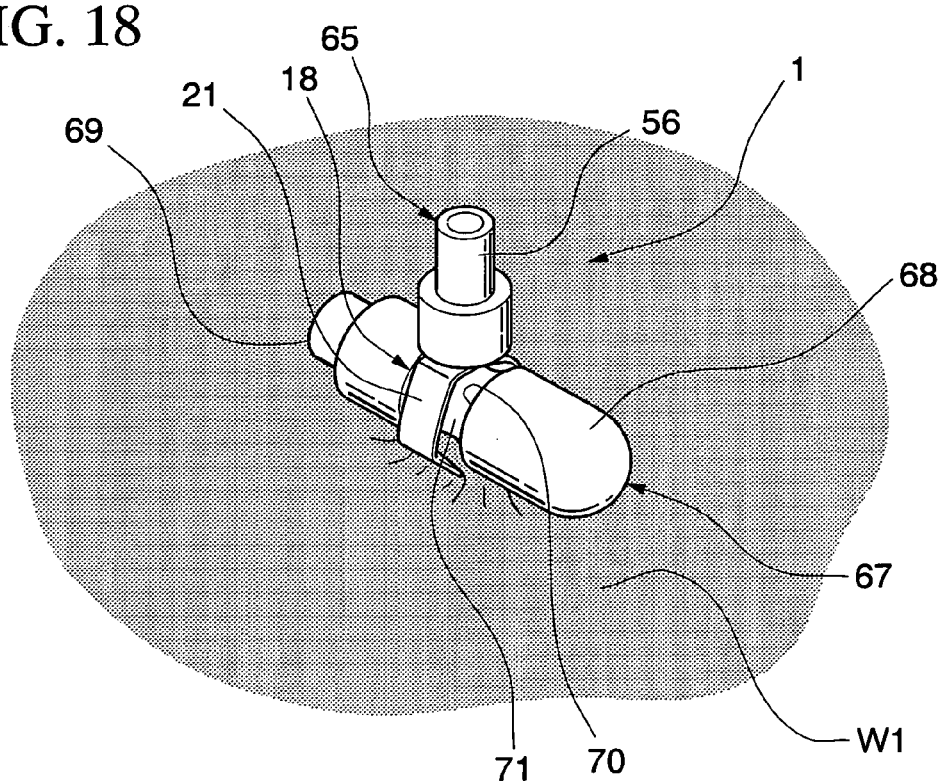

LIFTING METHOD FOR LESION AREA, AND ANCHORING DEVICE

BACKGROUND OF THE INVENTION

1. Field of the Invention

The present invention relates to a method of lifting a lesion area, and an anchoring tool used for lifting the lesion area, when a treatment is performed inside a living body.

2. Description of the Related Art

When a lesion area occurs inside a patient's body, the lesion area is resected or cauterized. At this time, there can be mentioned a case of incising the patient's body by means of a surgical operation, and an endoscopic treatment by using an endoscope inserted from the mouth or the anus. An example of a method of resecting a lesion area occurring in a hollow organ by an endoscope includes the methods shown in FIGS. 6 to FIG. 11 of Japanese Unexamined Patent Application, First Publication No. 2004-105247. Firstly, an overtube is inserted into the lesion area in the hollow organ, and then the endoscope is passed through the overtube. A clip attaching tool is passed through a channel of the endoscope, and a clip attached to the distal end of the clip attaching tool is attached to the lesion area. The endoscope is temporarily withdrawn from the overtube, and a magnetic anchor is passed from the distal side of the endoscope through the channel. The endoscope is again inserted into the overtube, and the magnetic anchor is hooked on the clip. A magnetic induction member is arranged outside the body, and the magnetic anchor is attracted by a magnetic force of the magnetic induction member. The lesion area is pulled via the clip, and lifted inside the hollow organ. The lifted lesion area is resected by a resection tool passed through the channel of the endoscope.

SUMMARY OF THE INVENTION

A lifting method for a lesion area according to a first aspect of the present invention includes: a step of inserting an endoscope from a natural opening into a hollow organ having a lesion area; a step of introducing an anchoring tool having a magnetic body and an anchor into the hollow organ, by using the endoscope; a step of anchoring the anchoring tool, by sequentially placing the anchor in a predetermined position around the lesion area, so as to arrange a plurality of the magnetic bodies around the lesion area; and a step of lifting a tissue including the lesion area, by attracting the magnetic bodies using the magnetic field generation tool arranged on the outside of the hollow organ.

An anchoring tool according to a second aspect of the present invention includes: a magnetic body inserted through a natural opening into a hollow organ having a lesion area, and attracted by a magnetic field generated outside of the hollow organ; an anchor inserted together with the magnetic body through the natural opening into the hollow organ, and placed on a tissue around the lesion area; and a positioning plate attached to the magnetic body or the anchor, and radially extended with the magnetic body or the anchor as the center.

A lifting method for a lesion area according to a third aspect of the present invention includes: a step of introducing an anchoring tool having a magnetic body and an anchor and provided with a positioning plate, into a hollow organ having a lesion area, by using a working channel inserted from a natural opening into the hollow organ; a step of anchoring a plurality of the anchoring tools inside the hollow organ, by measuring a distance from an outer edge of the lesion area using the plate, and sequentially placing the anchors at an approximately fixed distance from the outer edge of the lesion area, so as to arrange the magnetic bodies around the lesion area; and a step of lifting a tissue including the lesion area, by attracting the magnetic bodies using a magnetic field generation tool arranged on the outside of the hollow organ.

BRIEF DESCRIPTION OF THE DRAWINGS

FIG. 17 shows the anchoring tool projected from an insertion tube to drop a magnetic body.
FIG. 18 shows the magnetic body clamped by the clip, to anchor the anchoring tool.

DETAILED DESCRIPTION OF THE INVENTION

Hereunder is a detailed description of embodiments of the present invention. In the respective embodiments, the same reference symbols are used for the same components, and duplicate descriptions are omitted.

First Embodiment

Figure 1:
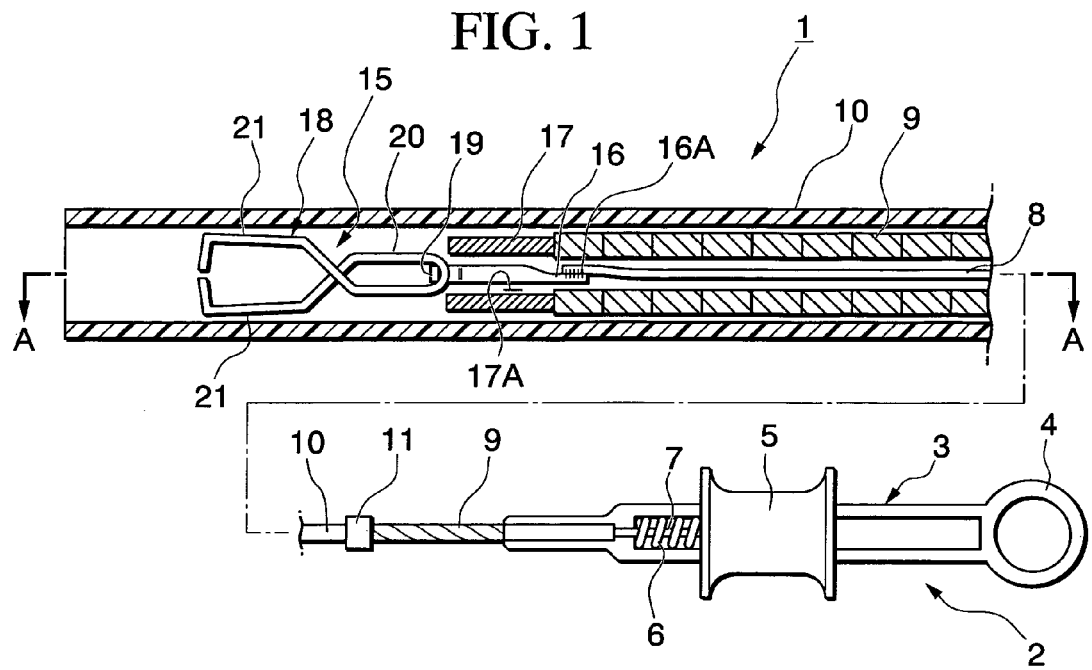
FIG. 1 shows a construction of an anchoring tool and an anchoring device according to the present embodiment.

FIG. 1 shows an anchoring tool and an anchoring device used in the present embodiment. The anchoring device 1 has an operation portion 2 operated by an operator. The proximal end of a main body 3 of the operation portion 2 is provided with a ring 4 which is hooked by a finger of an operator. The main body 3 is fitted with a slider 5 in a back-and-forth movable manner. The slider 5 is biased toward the distal end by a compression type coil spring 6. A pipe 7 is connected to the slider 5, and a wire is passed through the pipe 7. The wire is passed through a coil sheath 9 fixed to the distal end of the main body 3, in a back-and-forth movable manner. The coil sheath 9 is passed through an insertion tube 10, in a back-and-forth movable manner. The insertion tube 10 is made from a plastic such as a fluororesin or a polyethylene resin. The proximal end of the insertion tube 10 is provided with a grip 11 grasped by the operator. The insertion tube 10 and the coil sheath 9 are slender and flexible, and are inserted into a working channel of an endoscope (not shown). The wire 8 extended in the coil sheath 9 is fixed to the slider 5. The distal end of the wire 8 is welded to a connection plate 16 of an anchoring tool 15.

Figure 2:
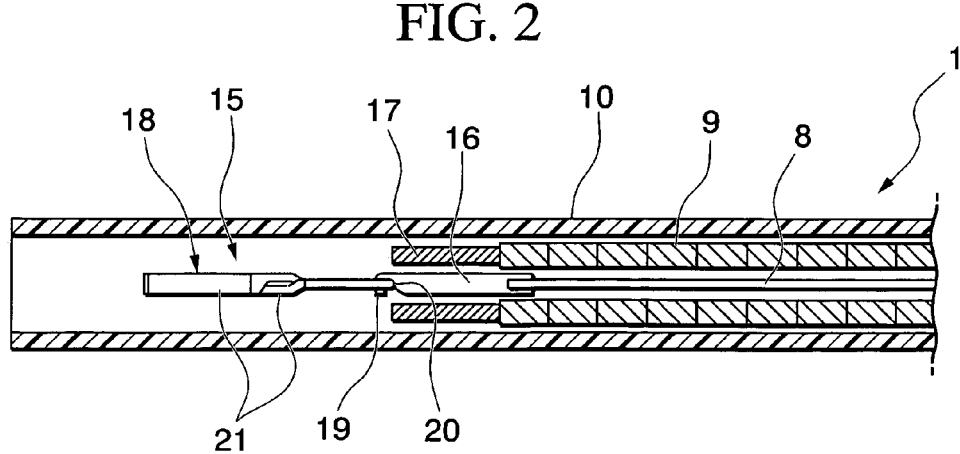
FIG. 2 is a cross-sectional view taken along the line A-A of FIG. 1.

As shown in FIG. 1 and FIG. 2, the anchoring tool 15 has the connection plate 16, a cylindrical magnetic body tube (magnetic body) 17 through which the connection plate 16 is passed, and a clip (anchor) 18. The distal end of the connection plate 16 is projected to the distal side of the magnetic body tube 17, where a hook 19 is formed. The hook 19 is engaged with a loop portion 20 of the clip 18. The clip 18 has a shape where the loop portion 20 is formed by bending the central portion of a slender member, and arm portions 21 are opened towards the distal end in a natural condition.

Here, the magnetic body tube 17 has an outer diameter greater than an inner diameter of the coil sheath 9. This magnetic body tube 17 is made from a magnet. The magnetic body tube 17 may be made from a soft magnetic body which is magnetized if a magnetic field is applied from the outside. The soft magnetic body (also called a soft magnetic material, or a soft type magnetic material) among magnetic bodies, has a property of losing its magnetism if a magnetic influence is removed. That is, it has a property of being magnetized (polarized) if it is put in a magnetic field, and substantially demagnetized if it is taken out from the magnetic field (the magnetic field is removed). As a material for such a soft magnetic body, there are known iron, pure iron, silicon iron, penmalloy iron, and the like.

Figure 3:
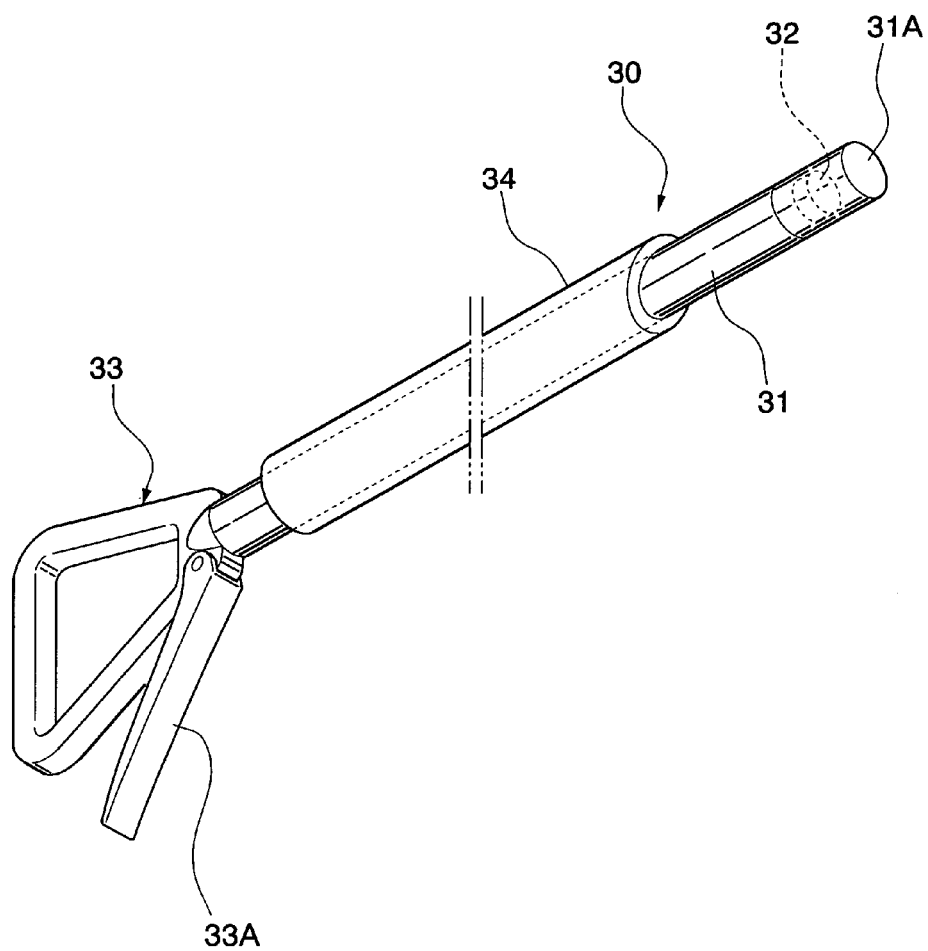
FIG. 3 is a perspective view showing a magnet forcep.

FIG. 3 shows a magnet forcep used in the present embodiment. The magnet forcep 30 serving as a magnetic field generation tool, has a tubular insertion portion 31 having the distal end closed by a cover 31A. A pusher rod (not shown) is inserted into the insertion portion 31. The distal end of the pusher rod is fixed with a magnet 32. The proximal end of the insertion portion 31 is provided with an operation portion 33. When a lever 33A of the operation portion 33 is operated, the magnet 32 in the insertion portion 31 can be brought closer to the cover 31A or apart from the cover 31A. The insertion portion 31 is passed through a cylindrical hard sheath 34. The detailed construction and the usage of the magnet forcep 30 are disclosed in U.S. patent application Ser. No. 11/076,662 by the present inventors. The contents disclosed in U.S. patent application Ser. No. 11/076,662 are incorporated in the present embodiment.

The operation of the present embodiment will be described.

Figure 4:
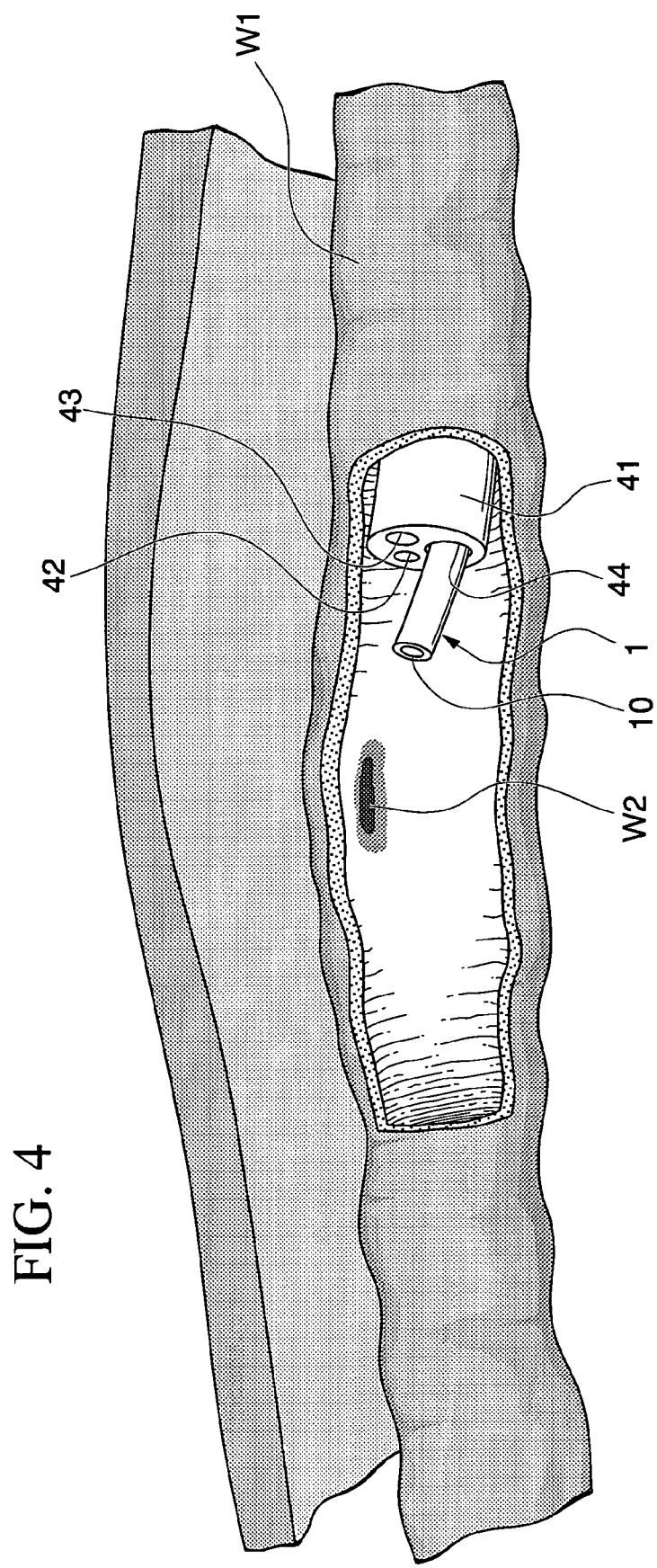
FIG. 4 shows an endoscope inserted into a hollow organ.

As shown in FIG. 4, an endoscope 41 is inserted from a natural opening in a living body (such as the mouth, the anus, a nostril, and an ear hole) into a hollow organ W1. While the inside of the hollow organ W1 is illuminated by an illuminating device 42 provided on the distal end of the endoscope 41, it is observed by an observation device 43, to confirm a lesion area W2 occurring inside of the hollow organ W1. An anchoring device 1 to which a first anchoring tool 15 is attached, is passed through a working channel 44 of an endoscope 41. The insertion tube 10 is fixed by grasping the grip 11 of the anchoring device 1 shown in FIG. 1, and the operation portion 2 is then pushed in. The coil sheath 9 and the anchoring tool 15 come out from the distal opening of the insertion tube 10. The clip 18 is faced to a tissue which is a predetermined distance apart from the periphery of the lesion area W2 of the hollow organ W1.

Figure 5:
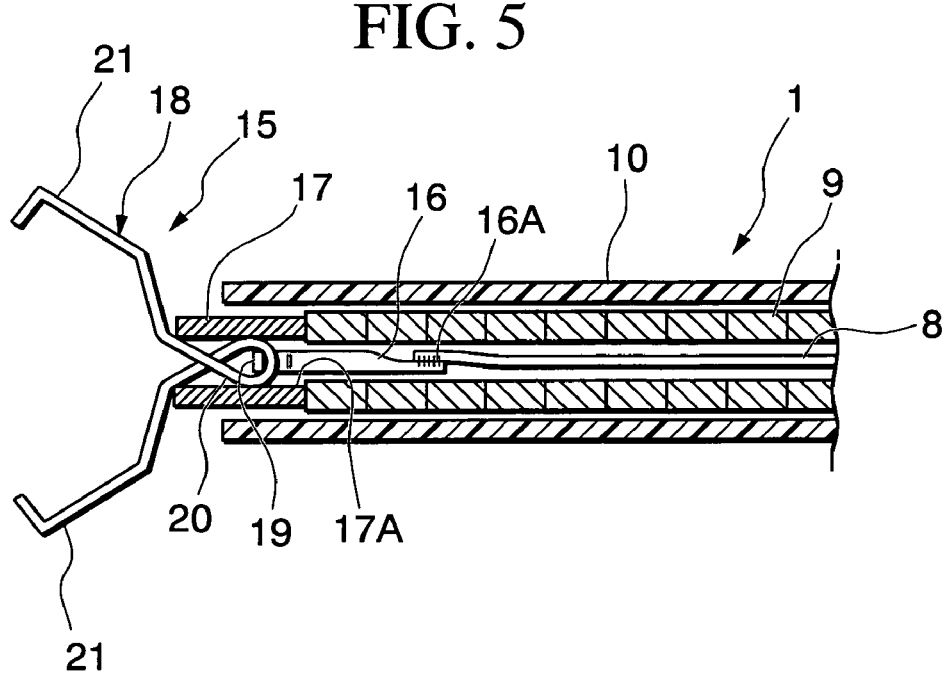
FIG. 5 is a cross-sectional view of the anchoring tool projected from the anchoring device.
Figure 6:
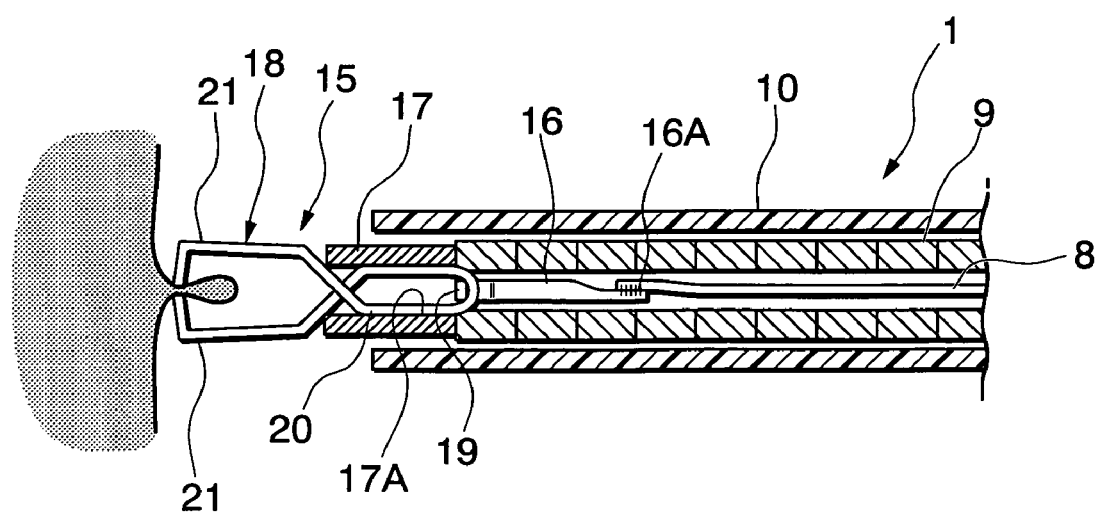
FIG. 6 shows a tissue clamped by a clip of the anchoring tool.

When the slider 5 is pulled, the wire 8 pulls the connection plate 16, and the loop portion 20 of the clip 18 is pulled into an inner hole 17A in the magnetic body tube 17. As shown in FIG. 5, the loop portion 20 is squashed by the magnetic body tube 17, and the pair of arm portions 21 are opened. While the arm portions 21 are opened, the clip 18 is pushed against the tissue. When the slider 5 is further pulled, the loop portion 20 is further pulled into the magnetic body tube 17, and the clip is closed, so that the living tissue is clamped by the clip 18. Finally, the curvature of the hook 19 formed at the distal end of the connection plate 16 is changed and straightened. As a result, the engagement of the connection plate 16 and the loop portion 20 is released, thus separating the anchoring tool 15 and the anchoring device 1. When the coil sheath 9 and the insertion tube 10 are pulled back from the endoscope 41, the anchoring tool 15 is anchored while clamping the tissue. Since the clip 18 is fitted into the magnetic body tube 17, it remains closed. Other connection methods for the anchoring tool 15 and the wire 8, and further details of the anchoring procedure are disclosed in US Patent Publication No. 2002/0173805 by the applicants of the present invention. The contents disclosed in US Patent Publication No. 2002/0173805 are incorporated in the present embodiment.

Figure 7:
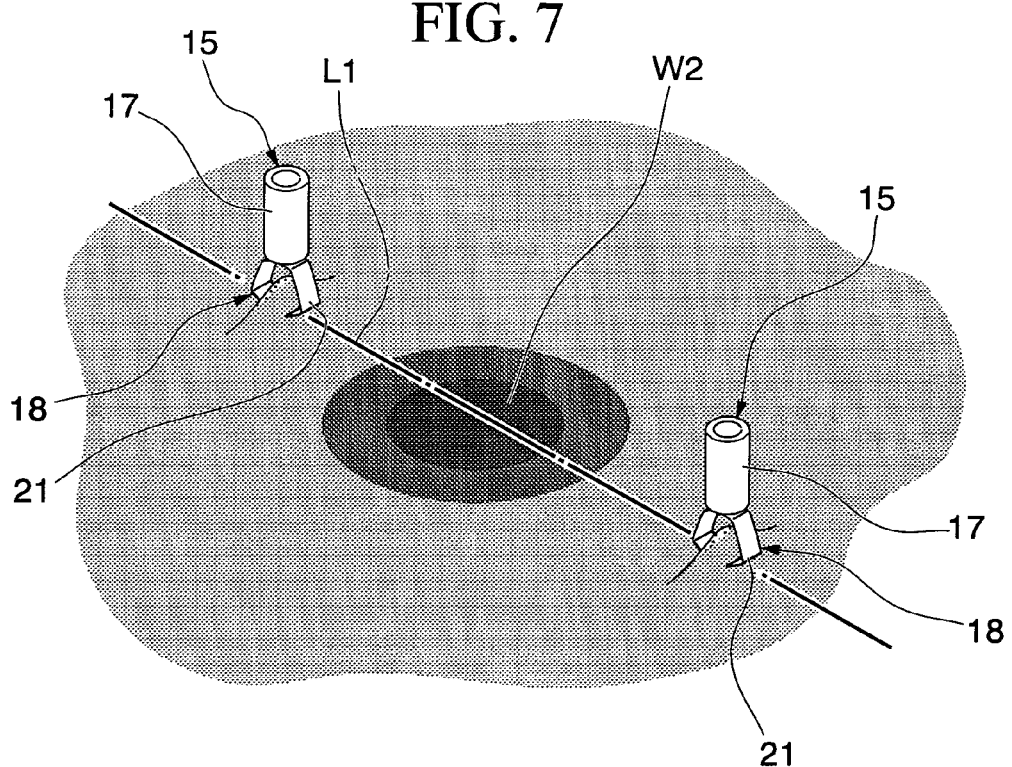
FIG. 7 shows anchor positions for when two anchoring tools are arranged.
Figure 8:
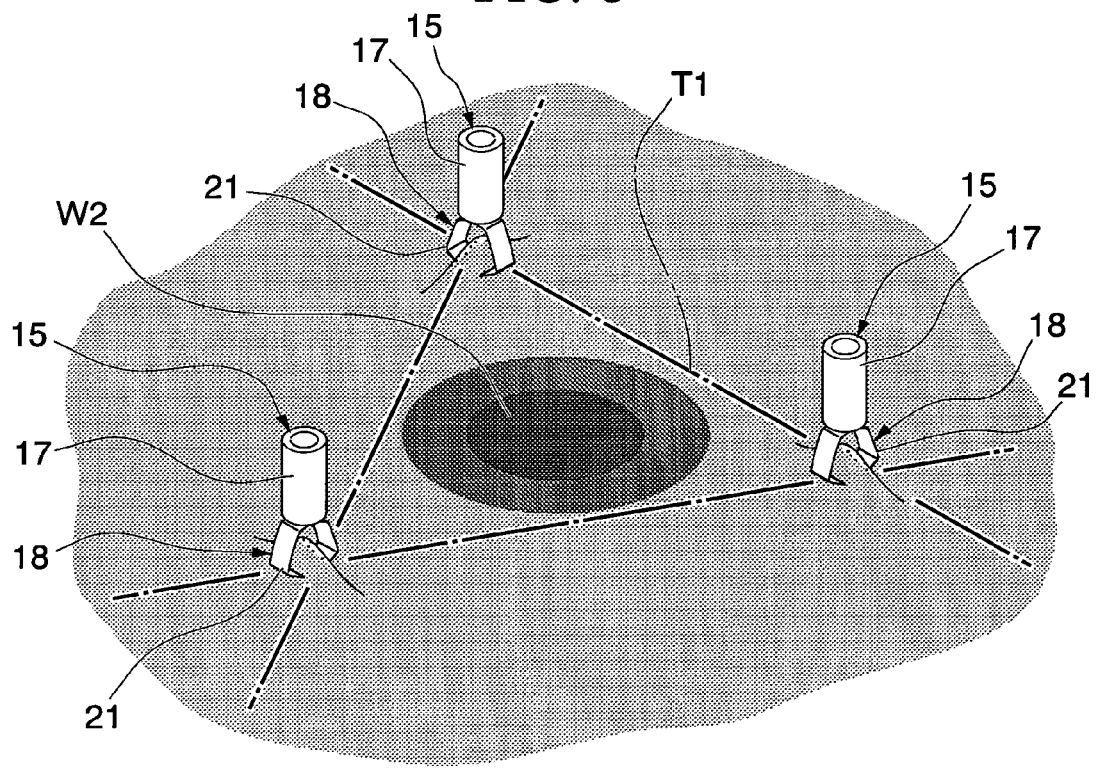
FIG. 8 shows anchor positions for when three anchoring tools are arranged.

Next, a second anchoring tool 15 is anchored around the lesion area W2. Another anchoring device 1 to which is attached the second anchoring tool 15 is newly passed through the working channel 44 of the endoscope 41. Here, FIG. 7 shows an arrangement in a case where only two anchoring tools 15 are anchored. The two anchoring tools 15 are sequentially anchored so that they are on either side of the lesion area W2, and an imaginary line L1 linking the clips 18 passes over the lesion area W2. FIG. 8 shows an arrangement in a case where three anchoring tools 15 are anchored. The three anchoring tools 15 are sequentially anchored so that at least a part of the lesion area W2 is within an imaginary triangle T1 having the anchor positions of the clips 18 as the apexes. Moreover, when three or more anchoring tools 15 are anchored, a plurality of anchoring tools 15 are sequentially anchored so that at least a part of the lesion area W2 is within a polygon formed by sides of imaginary lines linking anchor positions of adjacently anchored pairs of anchoring tools 15.

Figure 9:
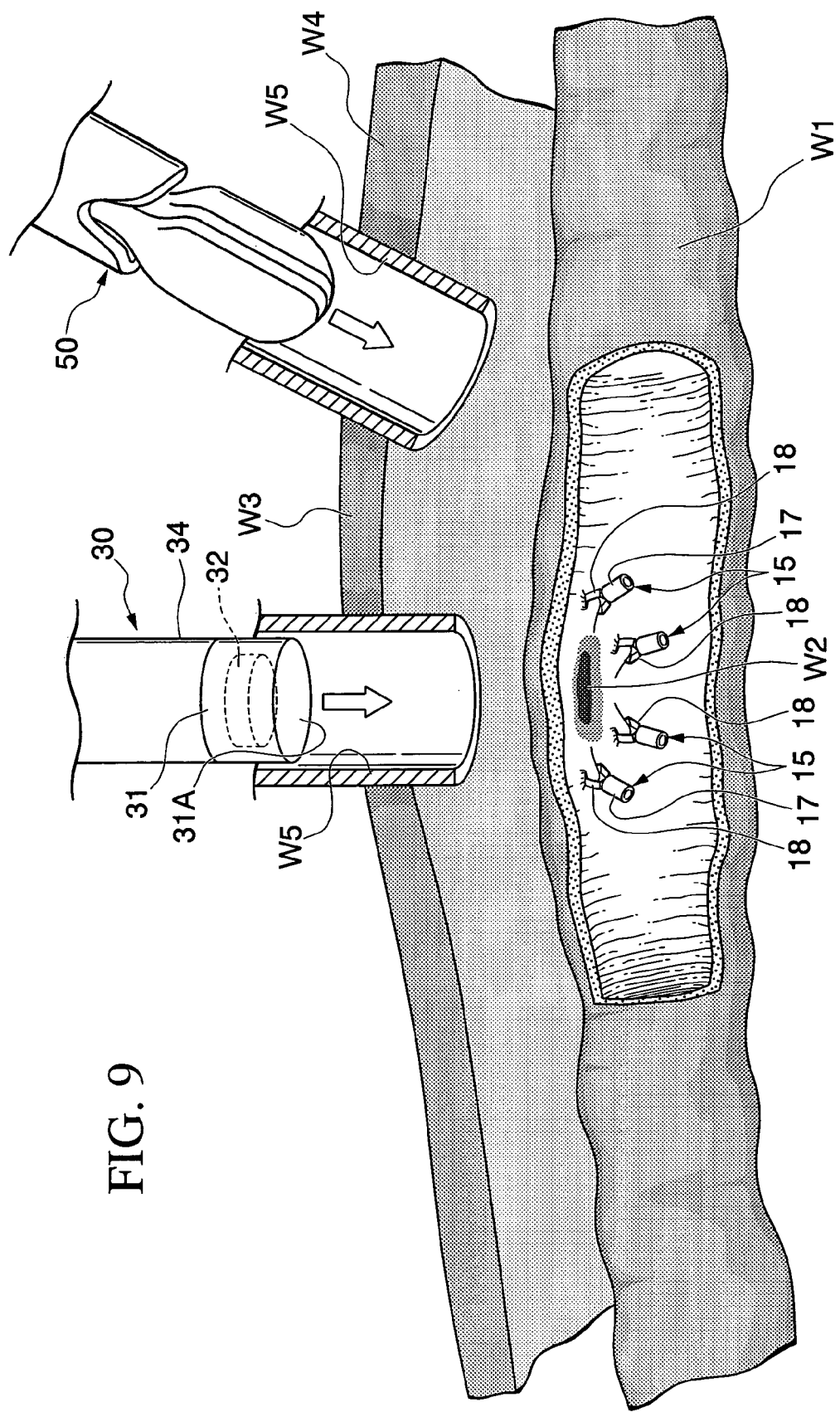
FIG. 9 shows four anchored anchoring tools.

After a necessary number of anchoring tools 15 are anchored, the endoscope 41 is withdrawn from the hollow organ W1. As shown in FIG. 9, two perforations are formed in the vicinity of the lesion area W2, in the abdominal wall W4, and forcep ports W5 are inserted therein respectively. In FIG. 9, four anchoring tools 15 are anchored so as to surround the lesion area W2, at approximately the same distance from the lesion area W2. The lesion area W2 is within a quadrangle (polygon) formed by imaginary lines linking anchor positions of adjacent pairs of anchoring tools 15.

Figure 10:
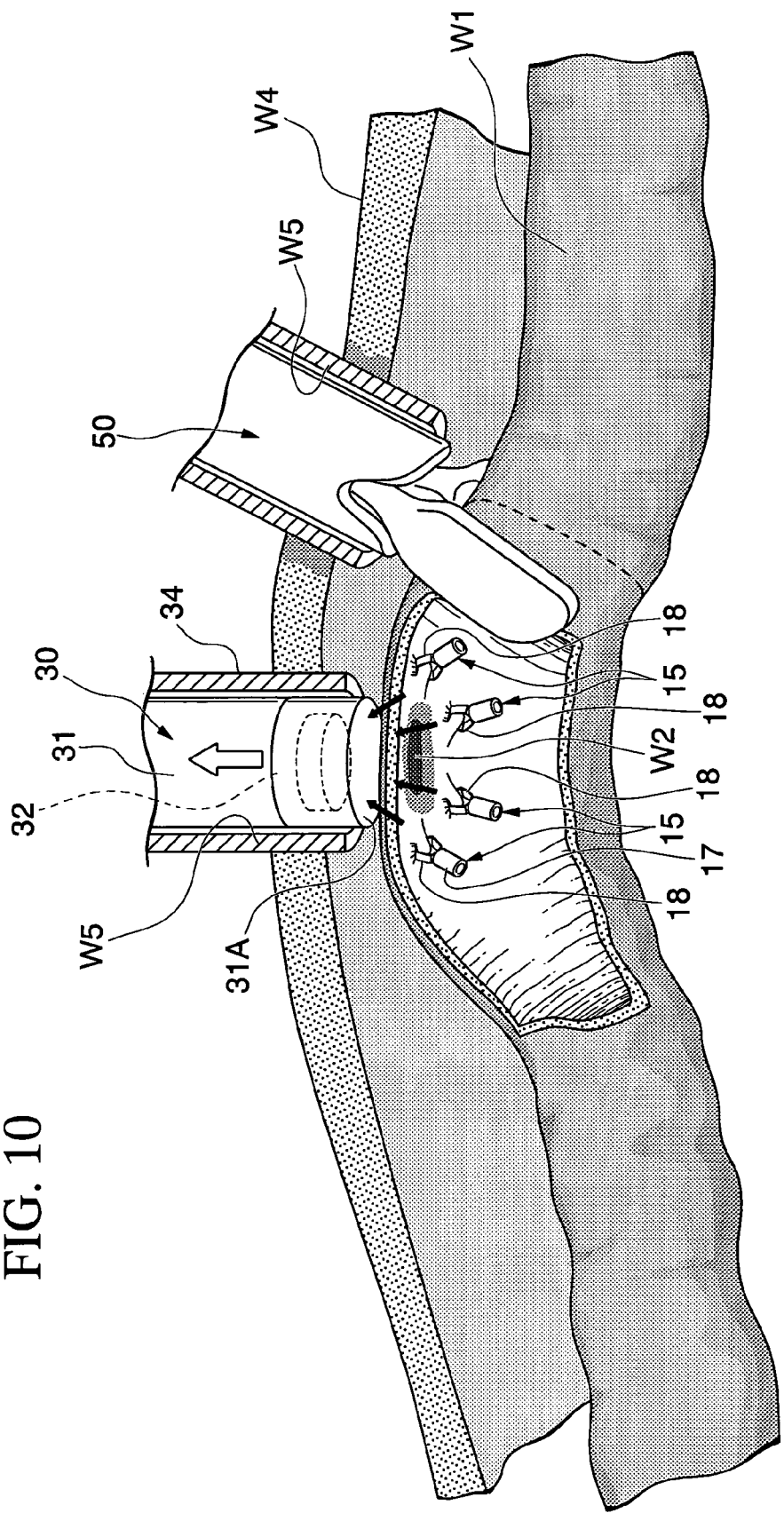
FIG. 10 shows a lifted tissue including a lesion area.

The magnet forcep 30 is inserted into the first forcep port W5, and an incision forcep 50 is inserted into the second forcep port W5. By pulling the lever 33A of the operation portion 33 of the magnet forcep 30 shown in FIG. 3, the magnet 32 is brought closer to the cover 31A on the distal end. As shown in FIG. 10, due to the magnetic field of the magnet 32 of the magnet forcep 30, all magnetic body tubes 17 are attracted, and all anchoring tools 15 are moved toward the magnet forcep 30, so that the tissue surrounded by the anchoring tools 15 is pulled out toward the magnet forcep 30. Since the hollow organ W1 comes into a posture such that the periphery of the lesion area W2 is projected toward the abdominal wall W4 (condition where the position of the tissue including the lesion area W2 is displaced to the abdominal cavity W4 side from the position in a natural condition (condition of being lifted to the abdominal cavity W4 side)), the incision forcep 50 is inserted from the second forcep port W5, and at an outer periphery of the anchor positions of the anchoring tools 15, the curved portion of the hollow organ W1 which has been pulled out (the portion shown by broken lines in FIG. 10) is resected. The tissue including the lesion area W2 is cut out, the cut out tissue is taken out from the forcep port W5 and the remaining hollow organ W1 is sutured.

In the present embodiment, since a plurality of anchoring tools 15 having the magnetic body tubes 17 are anchored around the lesion area W2, the range of the lesion area W2 becomes clear, and there is no need to depend on measurement by eye as in the conventional manner. Furthermore, since the magnetic body tubes 17 are attracted by the magnet 32, and the tissue including the lesion area W2 is pulled out toward the abdominal wall W4 side, the lesion area W2 can be reliably isolated from organs other than the hollow organ W1 including the lesion area W2, and other tissues of hollow organs, thus facilitating the resection. By resecting the outside of the anchoring tools 15, the outside of the lesion area W2 can be reliably incised. Since the lesion area W2 is not scratched nor damaged, the lesion area W2 can be used for subsequent diagnosis. Since a plurality of anchoring tools 15 are anchored, then when viewed as a whole, the contact area of the tissue and the clips 18 of the anchoring tools 15 becomes large, and the load on the hollow organ W1 can be reduced. When a plurality of anchoring tools 15 are anchored, there is no need to pull out the endoscope 41 at each time. Hence the manipulation time can be shortened.

Moreover, by forming the magnetic body tube 17 (magnetic body) from a soft magnetic body, the plurality of magnetic bodies anchored around the lesion area W2 can be demagnetized after removal from the magnet. Since substantially no magnetic force remains, the plurality of magnetic bodies can be kept from being attracted to each other due to residual magnetism.

Second Embodiment

Figure 11:
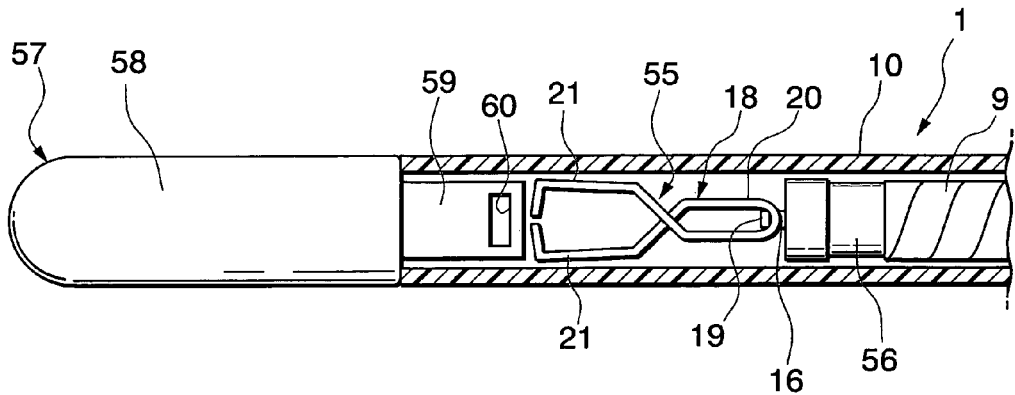
FIG. 11 shows a construction of an anchoring tool and an anchoring device.

FIG. 11 shows an anchoring tool and an anchoring device used in the present embodiment. The distal end of the anchoring device 1 is attached with an anchoring tool 55. The anchoring tool 55 includes a connection plate 16, a tube 56, a clip 18, and a magnetic body 57. The connection plate 16 is welded to a wire 8 (refer to FIG. 1), and is led out through the cylindrical tube 56 to the distal end of the tube 56. The distal end of the connection plate 16 becomes a hook 19 which latches the loop portion 20 of the clip 18. The magnetic body 57 is fitted into the opening of the insertion tube 10 from the distal end. In the magnetic body 57, a plate-like engagement portion 59 is extendingly provided from the proximal end of a main body 58. An outer diameter of the main body 58 is greater than an inner diameter of the insertion tube 10, and is approximately same as the outer diameter of the insertion tube 10. The engagement portion 59 is loosely fitted into the inner circumference of the insertion tube 10 by means of a press fit or the like. In the engagement portion 59, an elongate hole 60 is opened so that the arm portions 21 of the clip 18 can be inserted therein. This magnetic body 57 is made from a magnet or a soft magnetic body.

Figure 12:
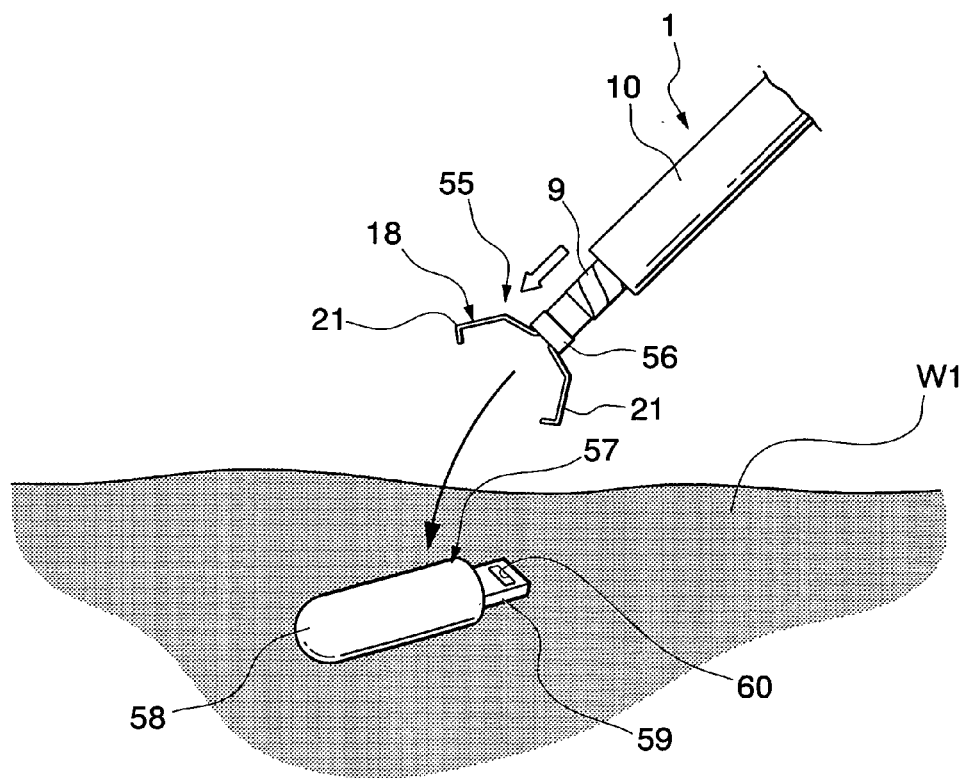
FIG. 12 shows the anchoring tool projected from an insertion tube to drop a magnetic body.
Figure 13:
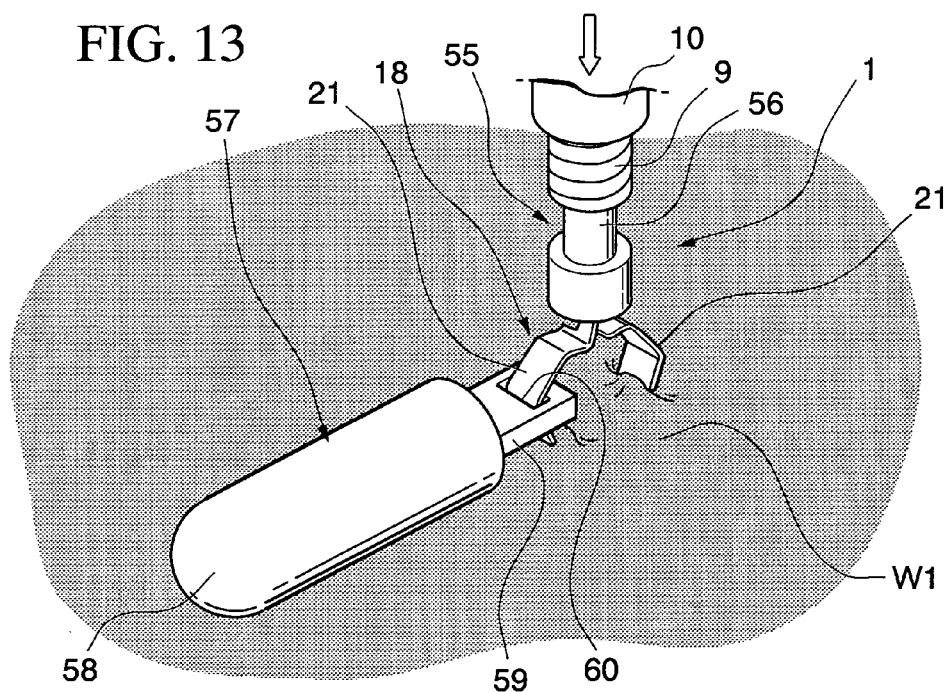
FIG. 13 shows the magnetic body hooked on the clip.
Figure 14:
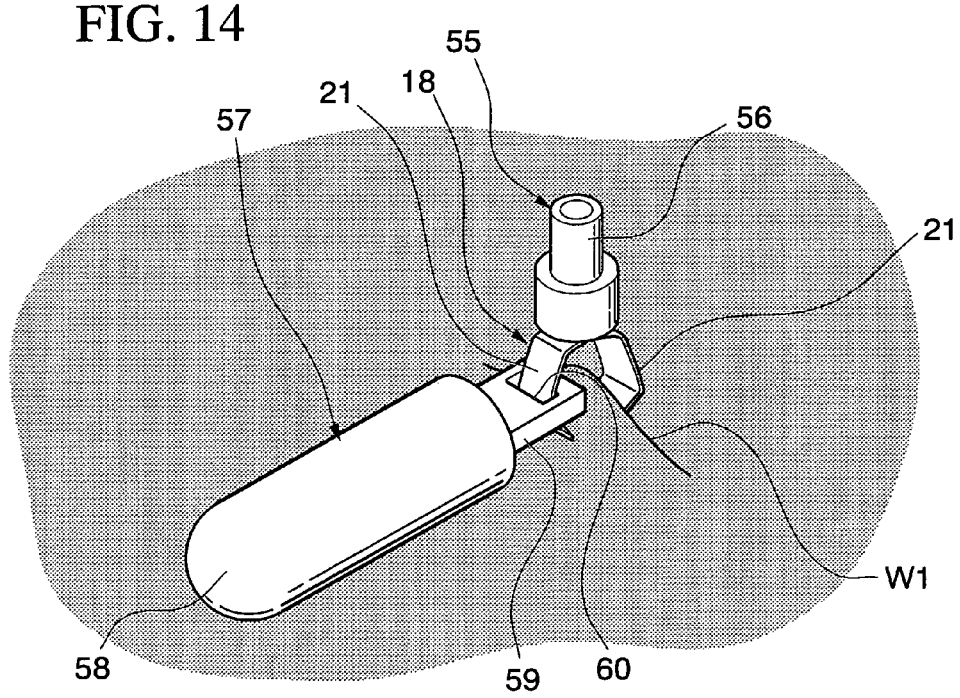
FIG. 14 shows the anchored anchoring tool.
Figure 15:
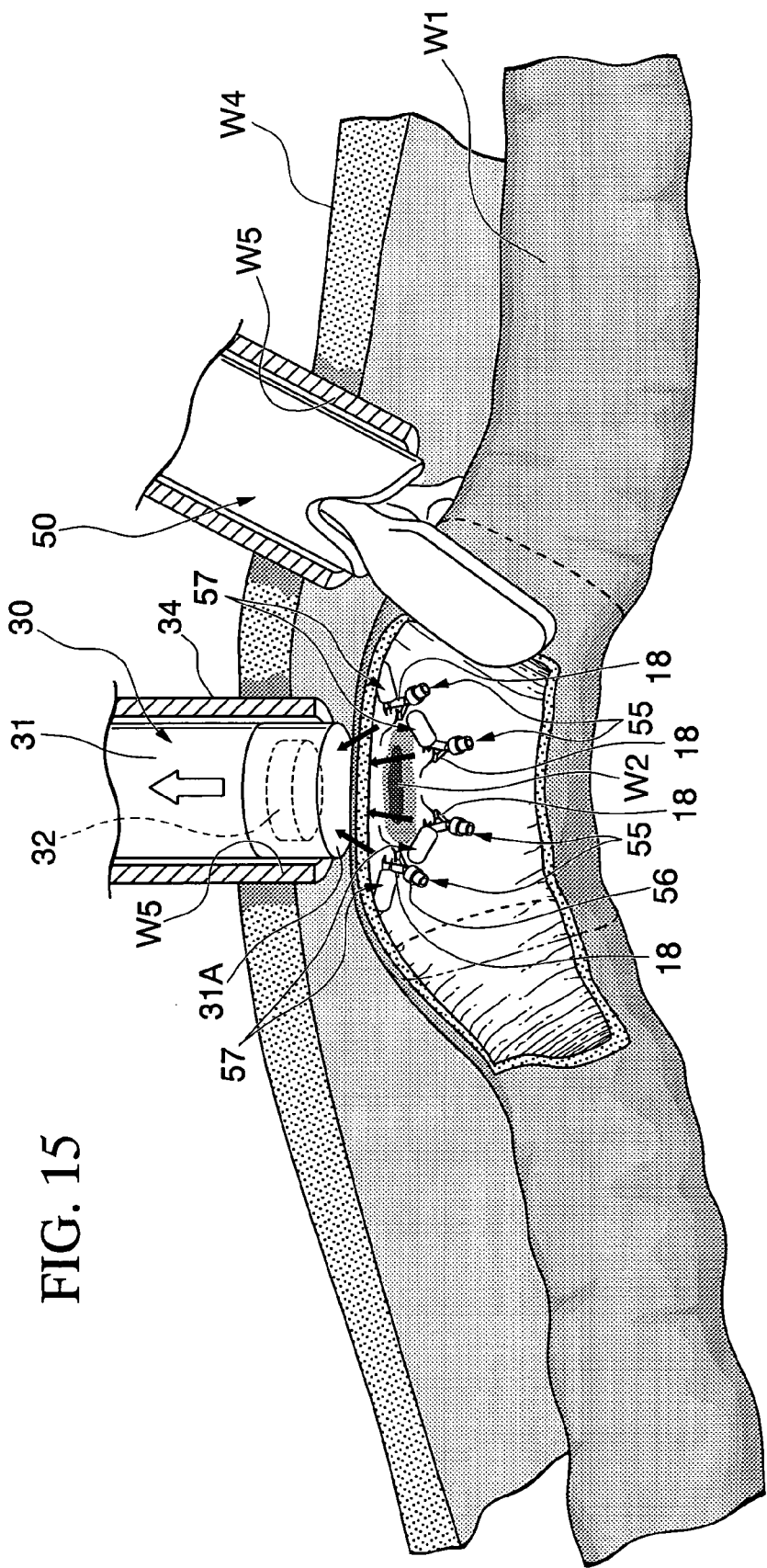
FIG. 15 shows a lifted tissue including a lesion area.

When the lesion area W2 is lifted to perform a treatment, a plurality of anchoring tools 55 are sequentially anchored inside the hollow organ W1. The anchoring device 1 attached with a first anchoring tool 55 is passed through the working channel 44 of the endoscope 41. After the anchoring device 1 is guided to around the lesion area W2, the coil sheath 9 is moved forward with respect to the insertion tube 10. As shown in FIG. 12, the clip 18 is moved forward together with the coil sheath 9, to drop the magnetic body 57 from the insertion tube 10 onto the inside of the hollow organ W1. Then the slider 5 is pulled to open the clip 18, and one arm portion 21 is inserted into the elongate hole 60 of the magnetic body 57. The magnetic body 57 is then engaged with the clip 18. As shown in FIG. 13, the clip 18 is pushed onto a tissue in the anchor position around the lesion area W2. When the slider 5 is pulled to close the clip 18, the arm portions 21 are placed thus clamping the tissue. When the slider 5 is further pulled, the curvature of the hook 19 formed at the distal end of the connection plate 16 is changed and straightened. As a result, the engagement of the connection plate 16 and the loop portion 20 is released, thus separating the anchoring tool 55 and the anchoring device 1. As shown in FIG. 14, the first anchoring tool 55 is anchored. Similarly to FIG. 7 and FIG. 8, this operation is repeated so that the second and subsequent anchoring tools 55 are anchored in respective positions around the lesion area W2. As shown in FIG. 15, when the magnet forcep 30 is brought closer from the abdominal wall W4 side to attract the magnetic bodies 57, the tissue including the lesion area W2 is lifted to the abdominal wall W4 side. The tissue including the lesion area W2 is then resected by the incision forcep 50, and is taken out to the outside of the body.

In the present embodiment, since the magnetic body 57 can be thickened to the same degree as the outer diameter of the insertion tube 10, a strong force can be applied to the magnetic body 57. If the force to attract the magnetic body 57 can be increased and the magnet forcep 30 is brought closer, the tissue including the lesion area W2 can be readily lifted. Since the contact area of each magnetic body 57 and the tissue can be enlarged, the load on the tissue can be reduced. Other effects are the same as those of the first embodiment.

Third Embodiment

Figure 16:
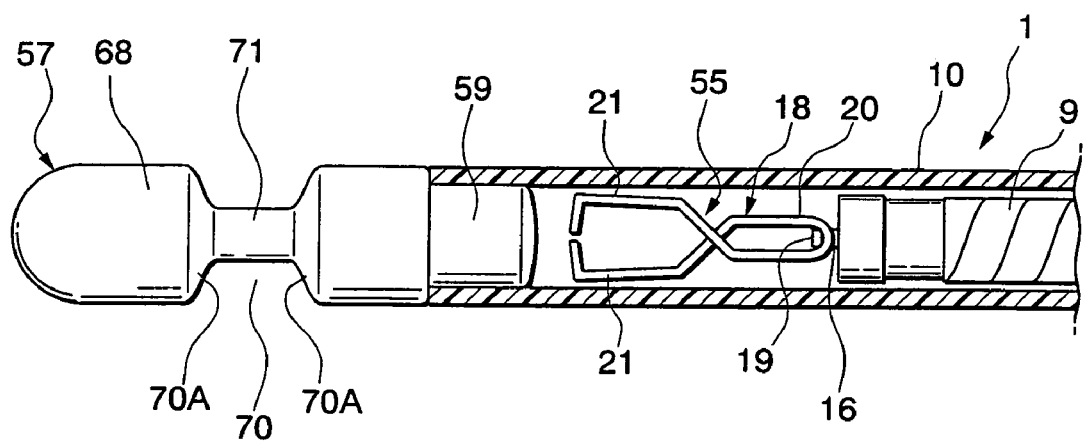
FIG. 16 shows a construction of an anchoring tool and an anchoring device.

FIG. 16 shows an anchoring tool and an anchoring device used in the present embodiment. An anchoring tool 65 has a connection plate 16, a tube 56, a clip 18, and a magnetic body 67. The magnetic body 67 is formed with a holding portion 69, a diameter of which is decreased at the proximal end of a main body 68. The outer diameter of the main body 68 is approximately the same as the outer diameter of the insertion tube 10. Its approximate center in the longitudinal direction is provided with a toroidal groove 70 toroidally around the circumferential direction, and a reduced diameter portion 71 is formed by the groove 70. The width of the groove 70 along the longitudinal direction of the main body 68 is a size such that the arm portions 21 of the clip 18 can be inserted. The thickness of the reduced diameter portion 71 is not more than the distance between the arm portions 21 when the clip 18 is closed. The groove 70 has an inclined face 70A where the longitudinal width is increased radially outward. The holding portion 69 can be inserted into the insertion tube 10, and is loosely fitted with the inner circumferential wall of the insertion tube 10. This magnetic body 67 is made from a magnet or a soft magnetic body.

Figure 19:
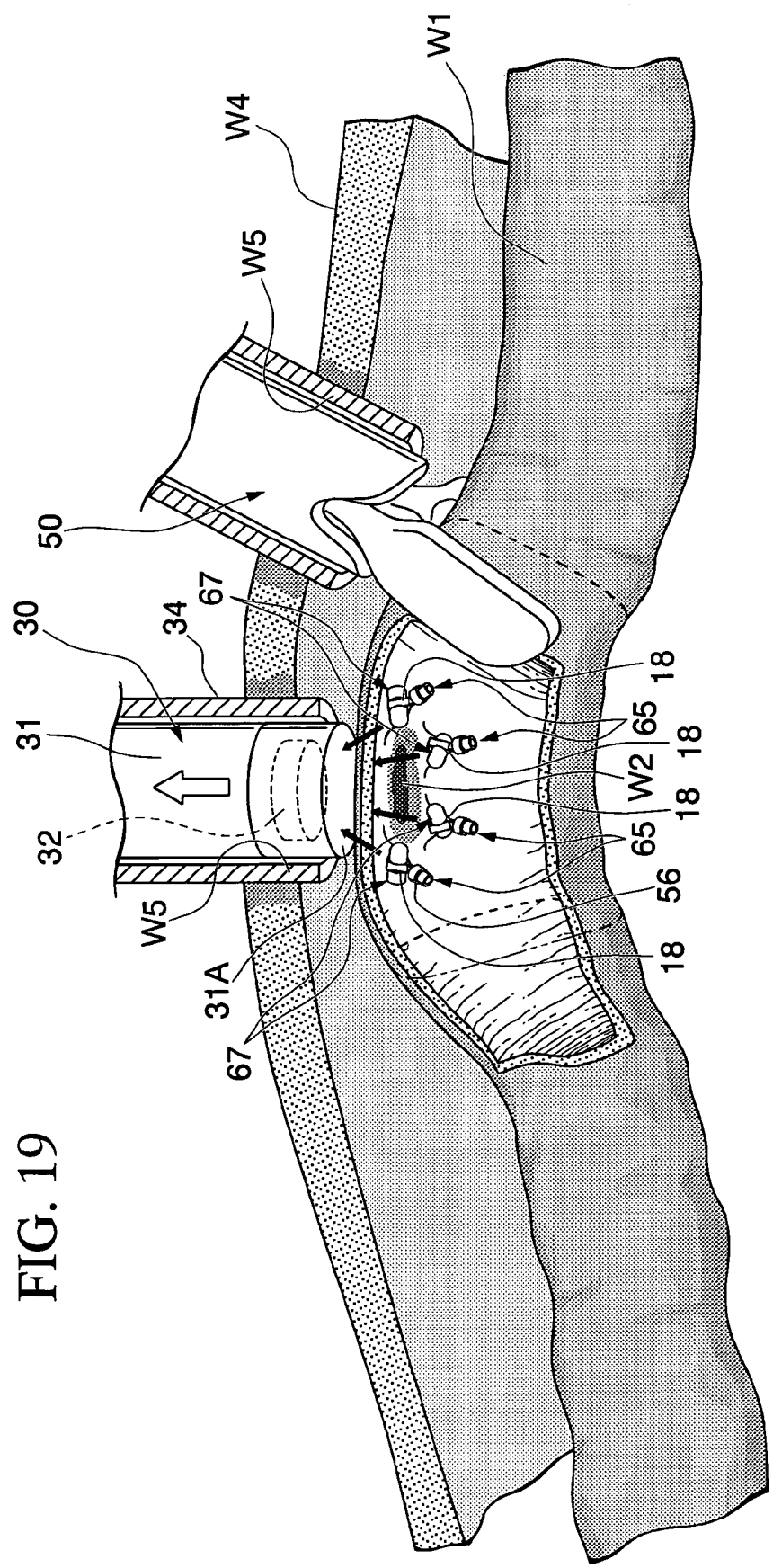
FIG. 19 shows a lifted tissue including a lesion area.

When the lesion area W2 is lifted to perform a treatment, a plurality of anchoring tools 65 are sequentially anchored inside the hollow organ W1. The anchoring device 1 is passed through the working channel 44 of the endoscope 41. After the anchoring device 1 enters to around the lesion area W2, the coil sheath 9 is moved forward with respect to the insertion tube 10. As shown in FIG. 17, the clip 18 is moved forward together with the coil sheath 9, to drop the magnetic body 67 from the insertion tube 10. After the magnetic body 67 is arranged in the anchor position by pushing using the clip 18 and the like, the slider 5 is pulled to open the clip 18. While the reduced diameter portion 71 of the magnetic body 67 is inserted between the pair of arm portions 21, the clip 18 is pushed onto a tissue in the anchor position. When the slider 5 is pulled to close the clip 18, the arm portions 21 are latched thus clamping the tissue. When the slider 5 is further pulled, the curvature of the hook 19 formed at the distal end of the connection plate 16 is changed and straightened. As a result, the engagement of the connection plate 16 and the loop portion 20 is released, thus separating the anchoring tool 65 and the anchoring device 1. As shown in FIG. 18, the first anchoring tool 65 is anchored. Similarly to FIG. 7 and FIG. 8, this operation is repeated so that the second and subsequent anchoring tools 65 are anchored in respective positions around the lesion area W2. As shown in FIG. 19, when the magnet forcep 30 is brought closer from the abdominal wall W4 side to attract the magnetic bodies 67, the respective anchoring tools 65 are moved toward the magnet forcep 30, and the tissue including the lesion area W2 is lifted to the abdominal wall W4 side. The tissue including the lesion area W2 is then resected by the incision forcep 50, and is taken out to the outside of the body.

In the present embodiment, since the anchoring tool 55 is anchored on the tissue while the longitudinal middle portion of the magnetic body 67 is clamped by the clip 18, the position of the magnetic body 67 is readily stabilized. Since the range including the lesion area W2 can be reliably specified, the resection position is readily specified. Other effects are the same as those of the second embodiment.

Fourth Embodiment

Figure 20:
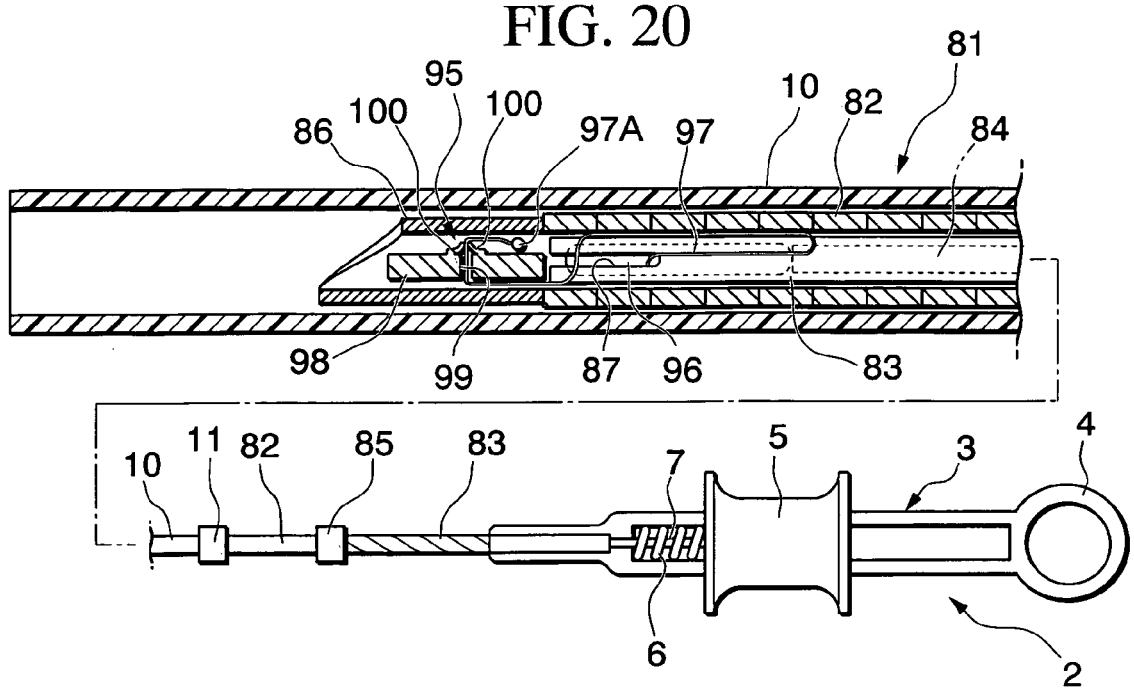
FIG. 20 shows a construction of an anchoring tool and an anchoring device.

FIG. 20 shows an anchoring tool and an anchoring device used in the present embodiment. In an anchoring device 81, an outer sheath 82 is inserted into the insertion tube 10 in a back-and-forth movable manner. An inner sheath 83 is inserted into the outer sheath 82 in a back-and forth-movable manner. The inner sheath 83 is arranged in the outer sheath 82 in the initial condition. A pusher 84 is inserted into the inner sheath 83 in a back-and-forth movable manner. The insertion tube 10, the outer sheath 82, the inner sheath 83, and the pusher 84 are slender and flexible. Grips 11 and 85 are respectively provided on the proximal end of the insertion tube 10 and the proximal end of the outer sheath 82 one for each, and can be operated to move back-and-forth by an operator. The inner sheath 83 is fixed to the main body 3 of the operation portion 2. The pusher 84 is fixed to the slider 5 of the operation portion 2. The distal end of the outer sheath 82 is fixed with a needle 86. The distal end of the inner sheath 83 is formed with a slit 87 along the lengthwise direction. Moreover, an anchoring tool 95 is contained in the outer sheath 82, the needle 86, and the inner sheath 83.

Figure 21:
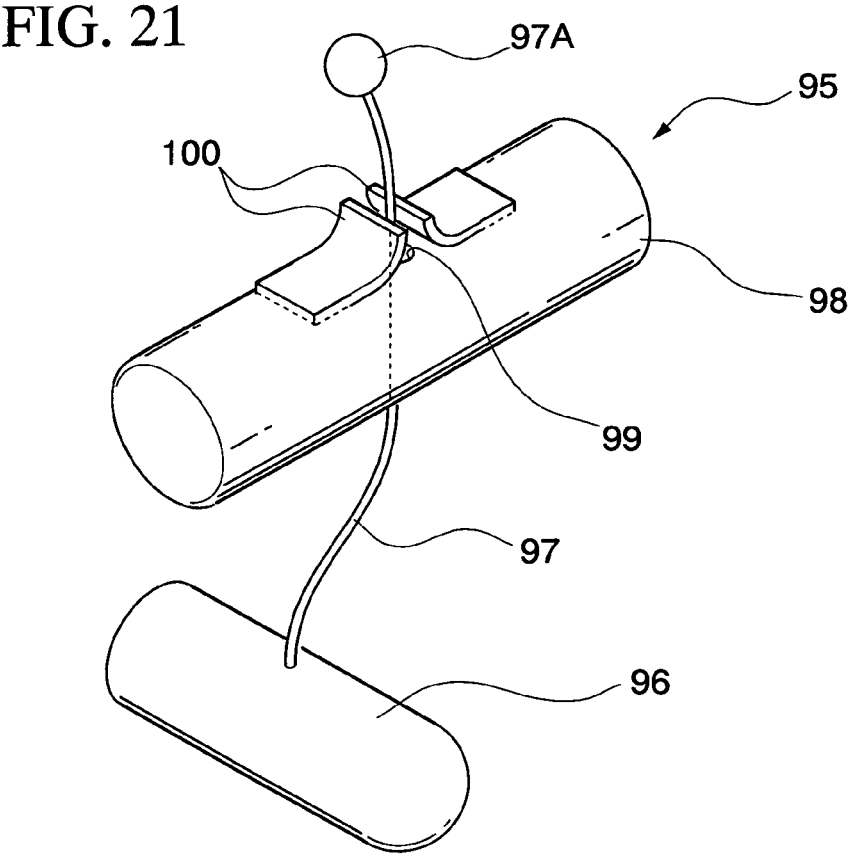
FIG. 21 shows a construction of the anchoring tool.

As shown in FIG. 20 and FIG. 21, the anchoring tool 95 has an anchor 96 contained in the inner sheath 83. The anchor 96 is inserted in parallel with the lengthwise direction of the inner sheath 83. To the central portion of the anchor 96 is fixed one end of a wire 97. The wire 97 is led out from the slit 87 of the inner sheath 83 into the outer sheath 82. The other end of the wire 97 is led around into the needle 86, and passed through a hole 99 in a magnetic body 98. The magnetic body 98 is a slender member inserted in parallel with the longitudinal direction of the needle 86. The hole 99 is formed in the center of the magnetic body 98. The position where an end 97A of the wire 97 passing through the hole 99 is led out, is provided with wire stoppers 100. A pair of wire stoppers 100 are provided facing each other so as to clamp the wire 97. The ends of the wire stoppers 100 are faced radially outward of the magnetic body 98. Therefore, the magnetic body 98 can be moved to the anchor 96 side with the end 97A of the wire 97 gripped. However when an attempt is made to move the anchor 96 toward the end of the wire 97, the wire stoppers 100 are caught on the wire 97, preventing the anchor 96 from being moved. The end 97A of the wire 97 is a knot for preventing the wire from going through. The arrangement of the anchor 96 and the magnetic body 98 may be visa-versa. However, if the arrangement is as shown in FIG. 20, the outer diameter of the magnetic body 98 can be enlarged. This magnetic body 98 is made from a magnet or a soft magnetic body.

Figure 22:
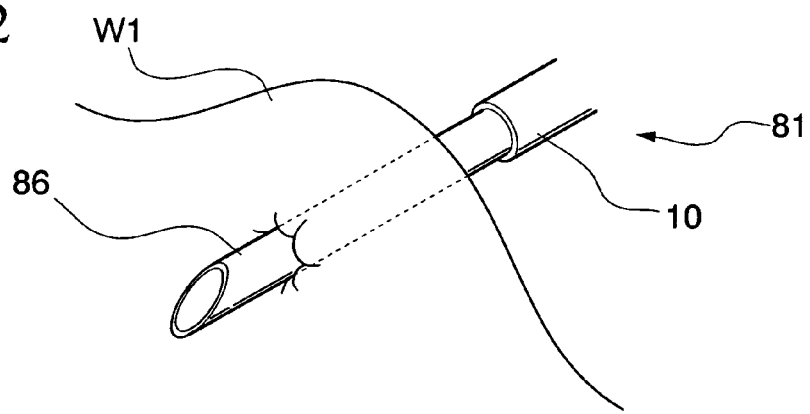
FIG. 22 shows a needle pierced through a tissue.
Figure 23:
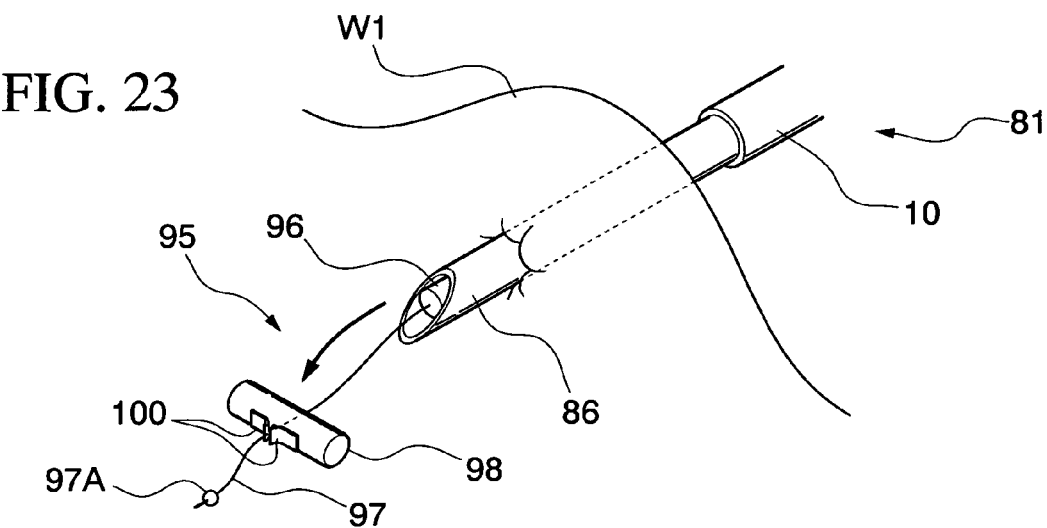
FIG. 23 shows a magnetic body pushed out from the needle.
Figure 24:
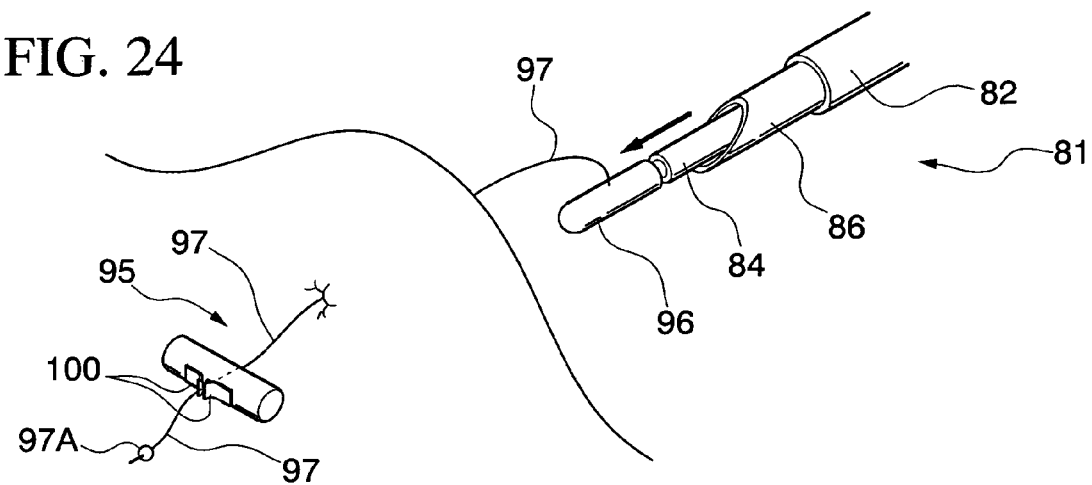
FIG. 24 shows the anchor pushed out after withdrawing the needle.

When the lesion area W2 is lifted to perform a treatment, a plurality of anchoring tools 95 are sequentially anchored inside the hollow organ W2. The anchoring device 81 attached with a first anchoring tool 95 is passed through the working channel 44 of the endoscope 41. The outer sheath 82 is moved forward by grasping the grip 85. As shown in FIG. 22, the needle 86 is pierced into the tissue in the anchor position. After the needle 86 is passed through the tissue, the operation portion 2 is pushed into the outer sheath 82 so as to move the inner sheath 83 forward. As shown in FIG. 23, the magnetic body 98 is pushed out from the needle 86 by the inner sheath 83. If the outer sheath 82 is pulled back, the needle 86 is withdrawn from the tissue. As shown in FIG. 24, the wire 97 is passed through the tissue. When the pusher 84 is moved forward, the anchor 96 is pushed out from the needle 86.

Figure 25:
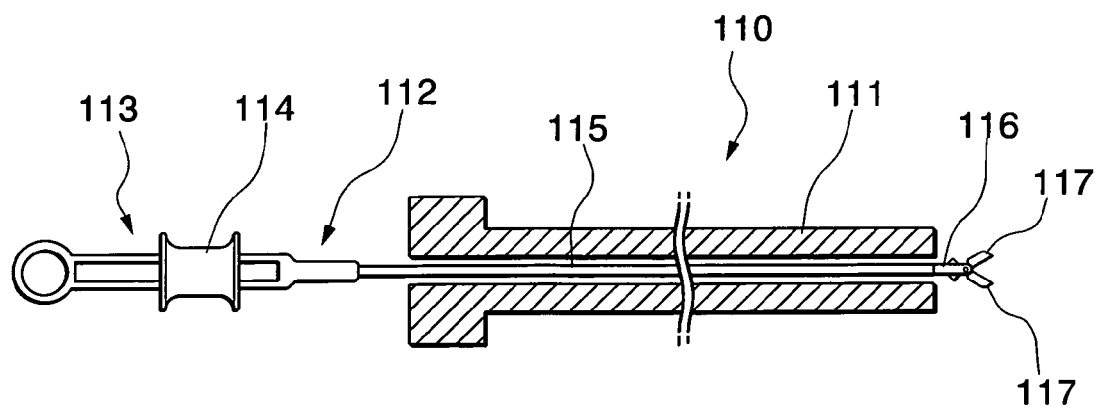
FIG. 25 is a cross-sectional view showing a construction of a clamp.
Figure 26:
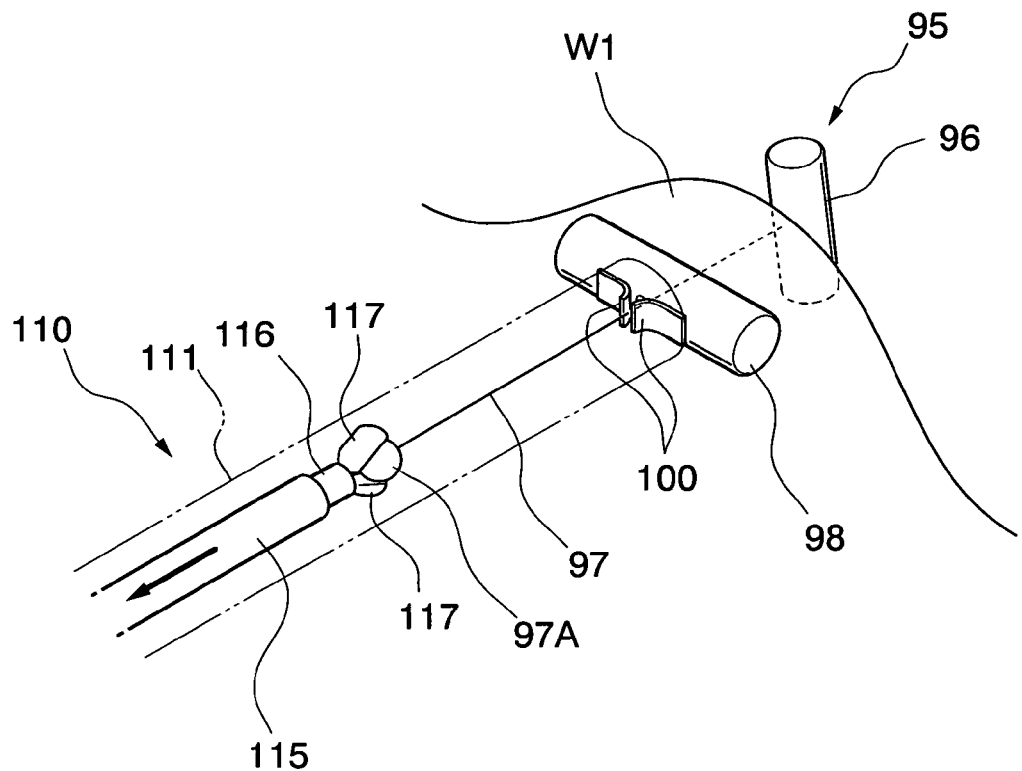
FIG. 26 shows the anchoring tool clamped by a clamp.

FIG. 25 shows a clamping device which can be used when clamping and placing the anchoring tool 95 onto the tissue. In the clamping device 110, a grasping forcep 112 is passed through a slender and flexible outer sheath 111 in a back-and-forth movable manner. The distal end of the sheath 115 is provided with a pair of grasping pieces 117 supported by a supporting member 116, in an openable/closable manner. When a slider 114 of the operation portion 113 is moved back-and-forth in the lengthwise direction, the pair of grasping pieces 117 at the distal end of the sheath 115 is opened/closed. This clamping device 110 is used by inserting through the working channel 44 of the endoscope 41.

In the clamping operation, the end 97A of the wire 97 is grasped by the pair of grasping pieces 117, and the grasping forcep 112 is moved backward while the outer sheath 111 is moved forward. The outer sheath 111 pushes the magnetic body 98 onto the tissue, and the wire 97 is pulled. Since the wire stoppers 100 of the magnetic body 98 allow the wire 97 to move in this direction, the anchor 96 is pulled by means of the wire 97, and the anchoring tool 95 is fastened so as to clamp the tissue between the magnetic body 98 and the anchor 96. If the clamping device 110 is removed after the pair of grasping pieces 117 are opened, the anchoring tool 95 is anchored on the tissue. Since the wire stoppers 100 of the magnetic body 98 do not allow the wire 97 to move in a direction to loosen the anchoring tool 95, then even if the clamping device 110 is removed, the anchor 96 and the magnetic body 98 maintain the placed condition on the tissue.

After the first anchoring tool 95 is anchored, these operations are repeated so that the second and subsequent anchoring tools 95 are anchored in respective positions around the lesion area W2. The second and subsequent anchoring tools 95 are anchored in similar positions and in a similar order to those of FIG. 7 and FIG. 8.

Figure 27:
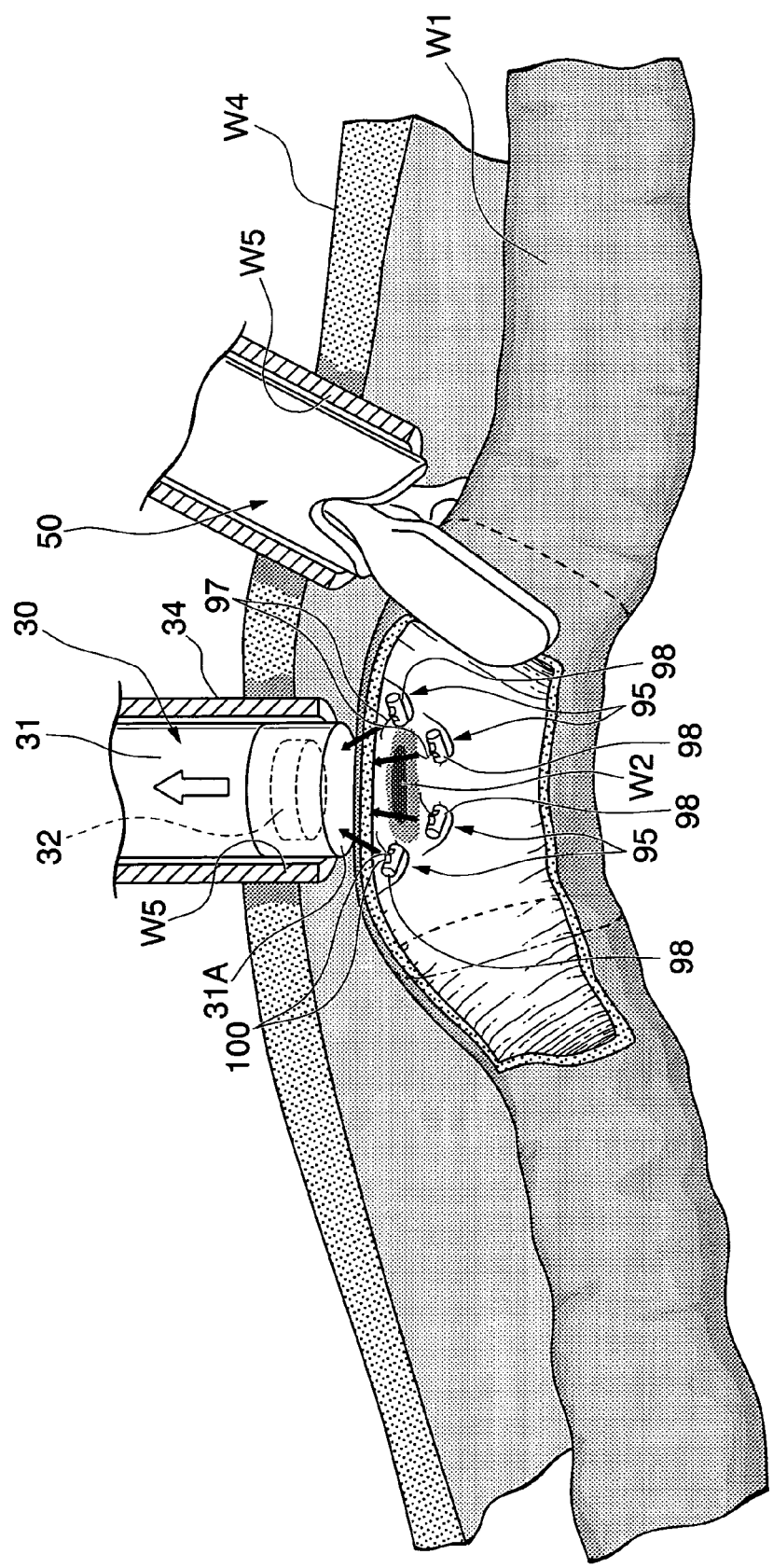
FIG. 27 shows a lifted tissue including a lesion area.

As shown in FIG. 27, when the magnet forcep 30 is brought closer from the abdominal wall W4 side to attract all the magnetic bodies 98, the respective anchoring tools 95 are moved toward the magnet forcep 30, and the tissue including the lesion area W2 is lifted to the abdominal wall W4 side. The tissue including the lesion area W2 is resected by the incision forcep 50, and is then taken out to the outside of the body.

In the present embodiment, since the construction is such that the anchoring tools 95 are passed through the tissue, the anchoring tools 95 are less likely to be dropped after they are anchored and while the treatment from lifting to resection is proceeded. It becomes possible to confirm that the anchoring tools 95 are reliably anchored by viewing through the observation device 43 (refer to FIG. 4) of the endoscope 41. Other effects are the same as those of the first embodiment.

Fifth Embodiment

Figure 28:
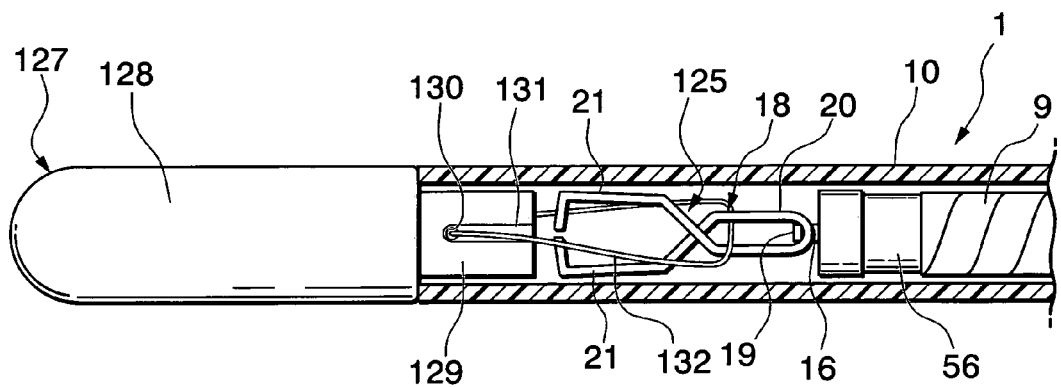
FIG. 28 shows a construction of an anchoring tool and an anchoring device.

FIG. 28 shows an anchoring tool and an anchoring device used in the present embodiment. An anchoring tool 125 has a connection plate 16, a tube 56, a clip 18, and a magnetic body 127. The magnetic body 127 is formed with a holding portion 129 having a small diameter at the proximal end of the main body 128, and is formed from a magnet or a soft magnetic body. The outer diameter of the main body 128 is approximately the same as the outer diameter of the insertion tube 10. The holding portion 129 can be inserted into the insertion tube 10, and is loosely fitted with the inner circumferential wall of the insertion tube 10. The holding portion 129 has a through hole 130 approximately orthogonal to the longitudinal direction. A groove 131 including the opening of the through hole 130 is formed up to the proximal end of the holding portion 129. A wire 132 is passed through the through hole 130. The wire 132 is in a torus shape passing from the through hole 130, through the groove 131, and through the inside of the loop portion 20 of the clip 18.

Figure 29:
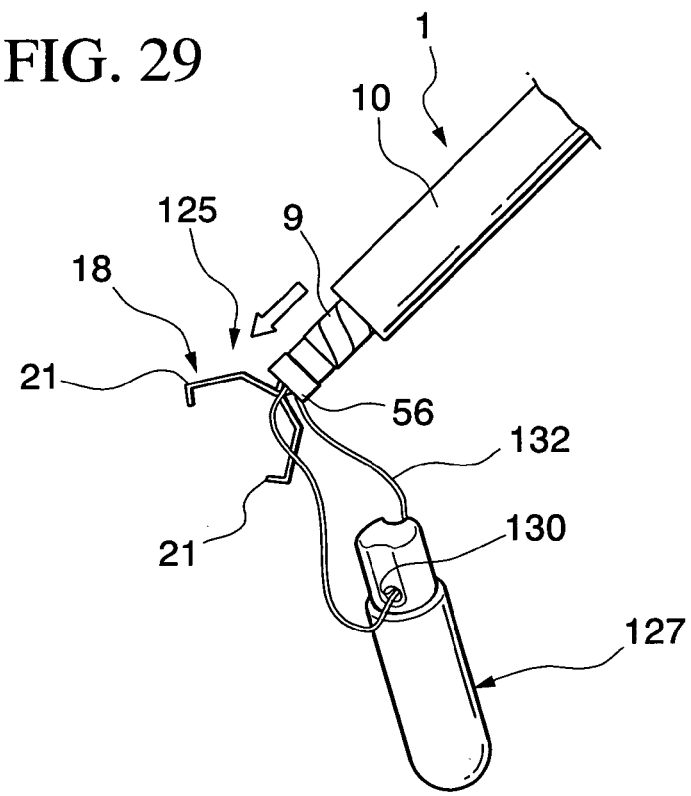
FIG. 29 shows the anchoring tool projected from an insertion tube to hang a magnetic body from the clip.
Figure 30:
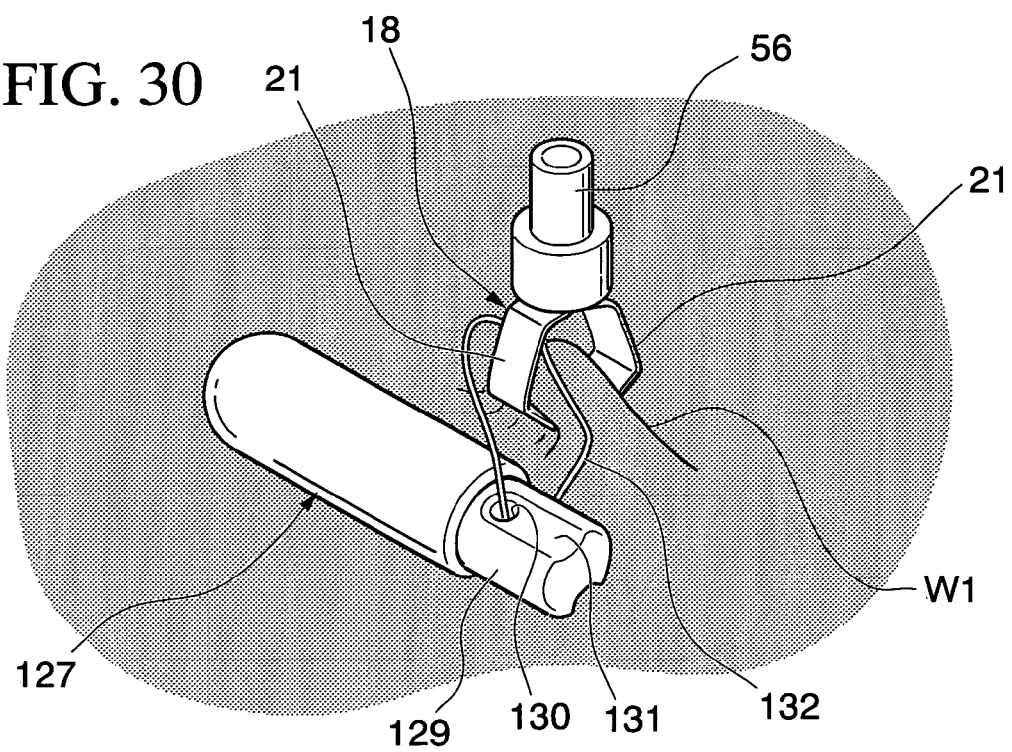
FIG. 30 shows an anchored anchoring tool.

When the lesion area W2 is lifted to perform a treatment, a plurality of anchoring tools 125 are sequentially anchored inside the hollow organ W1. The anchoring device 1 is passed through the working channel 44 of the endoscope 41. After the anchoring device 1 is guided to around the lesion area W2, the coil sheath 9 is moved forward with respect to the insertion tube 10. As shown in FIG. 29, the clip 18 is moved forward together with the coil sheath 9, to push the magnetic body 127 out from the insertion tube 10. Since the magnetic body 127 and the clip 18 are connected via the wire 132, the magnetic body 127 will not be dropped. The slider 5 is pulled to open the clip 18, and the clip 18 is pushed onto the tissue in the anchor position. When the slider 5 is pulled to close the clip 18, the arm portions 21 clamp the tissue. When the slider 5 is further pulled, the welded portion between the wire 8 and the connection plate 16 is broken. As shown in FIG. 30, the anchoring tool 125 is anchored in the anchor position. When the first anchoring tool 125 (magnetic body 127) is anchored, the operation up to here is repeated so that the second and subsequent anchoring tools 125 are sequentially anchored in respective positions around the lesion area W2.

Figure 31:
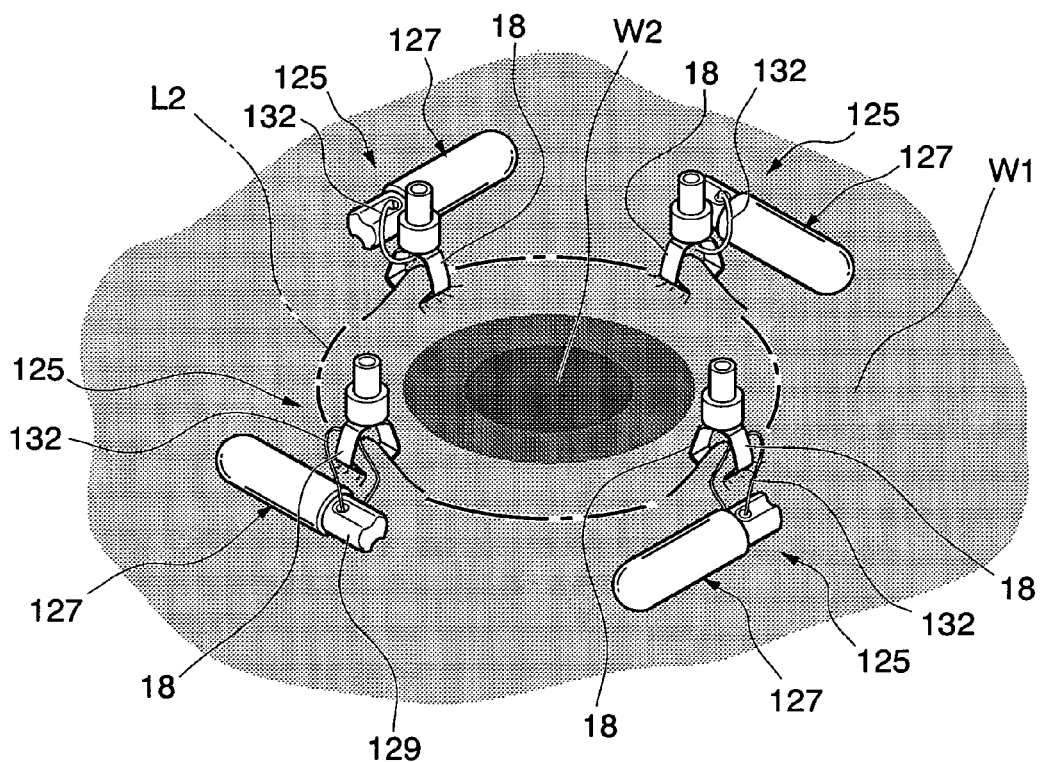
FIG. 31 shows four anchoring tools anchored around a lesion area.

For example, as shown in FIG. 31, four anchoring tools 125 are anchored around the lesion area W2, on the circumference of an imaginary circle L2 having the lesion area W2 as the center, at approximately equal intervals. In this anchoring tool 125, the clip 18 is fixed to the tissue, whereas the magnetic body 127 is connected to the clip 18 via the wire 132, and the position of the magnetic body 127 may be moved with respect to the placed position of the clip 18 in some cases. Therefore, the resection range is specified by the anchor positions of the clips 18. The anchoring tools 125 may be arranged in the arrangement as shown in FIG. 7 and FIG. 8.

Figure 32:
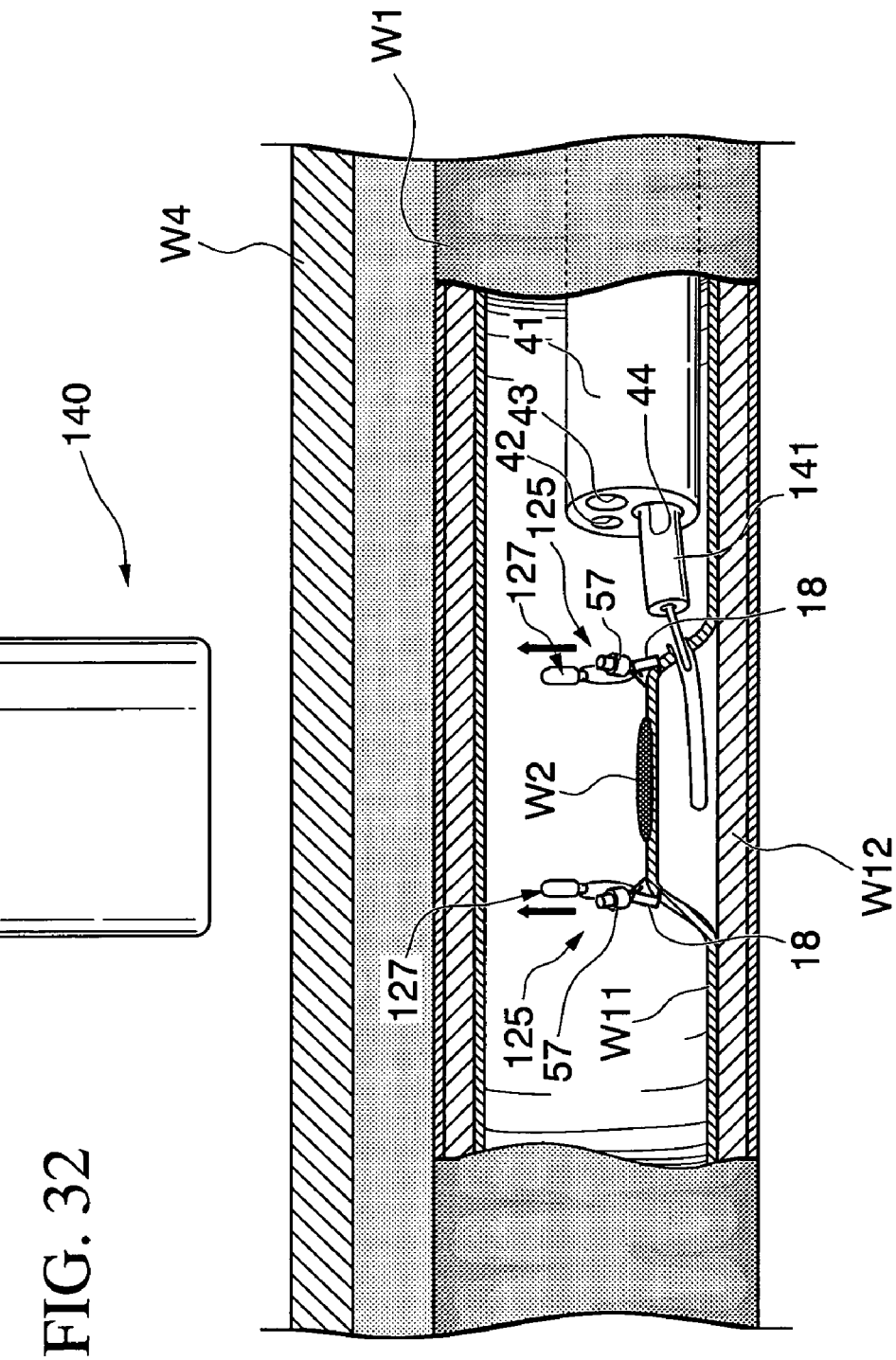
FIG. 32 shows a mucous membrane including the lesion area lifted to the inside of the hollow organ by attracting the anchoring tools.

As shown in FIG. 32, when the tissue including the lesion area W2 is to be lifted, a magnetic field generation tool 140 is brought closer to the lesion area W2 from the outside of the body. The magnetic field generation tool 140 may be a permanent magnet or an electromagnet. Approach of the magnetic field generation tool 140 is made from the opposite side of the lesion area W2, with reference to the center of the hollow organ W1. By means of the magnetic field formed by the magnetic field generation tool 140, the magnetic bodies 127 of the respective anchoring tools 125 are magnetized and attracted to the magnetic field generation tool 140. In the example shown in FIG. 32, since the lesion area W2 is formed in the mucous membrane W11, the mucous membrane W11 surrounded by the clips 18 is lifted from the muscularis W12 to the inside of the hollow organ W1. A resection tool 141 such as a high frequency scalpel is passed through the working channel 44 of the endoscope 41, and the periphery of the lifted mucous membrane W11 is resected. The magnetic field is then removed from the periphery of the magnetic bodies 127 by pulling the magnetic field generation tool 140 away, or the like. A treatment tool such as a snare is passed through the working channel 44 of the endoscope 41, and the resected mucous membrane including the lesion area W2 is collected.

Figure 33:
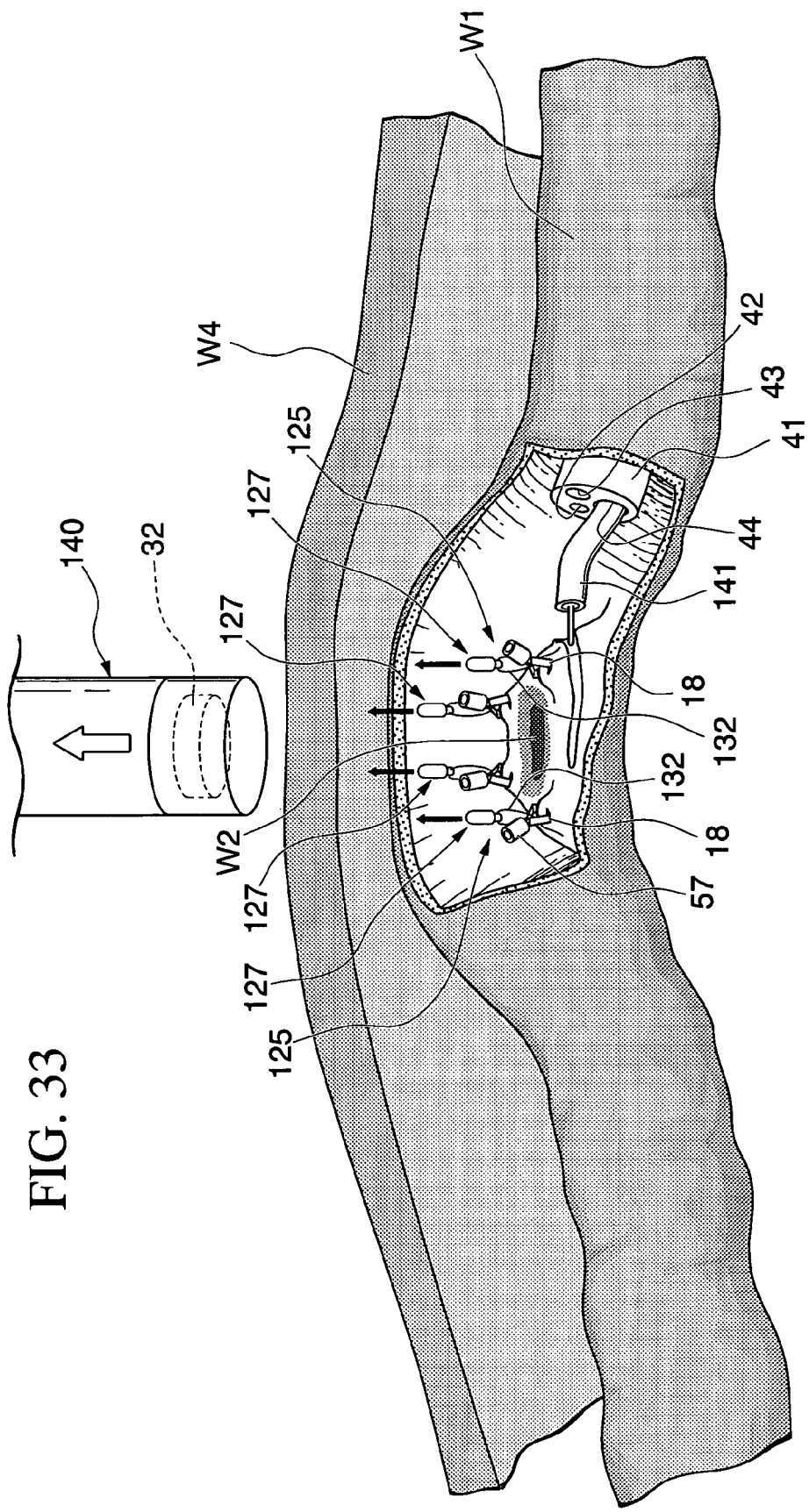
FIG. 33 shows an overall wall portion of the hollow organ lifted by attracting the anchoring tools.

FIG. 33 is an overall view of FIG. 32. As shown in FIG. 33, a plurality of clips 18 are arranged around the lesion area W2.

In the present embodiment, since the clip 18 and the magnetic body 127 are connected by the wire 132, there is no need for separately handling the clip 18 and the magnetic body 127. Since the tissue including the lesion area W2 is lifted to the inside of the hollow organ W1, resection of the lesion area W2 becomes possible without forming a perforation in the abdominal wall W4. The manipulation time can be shortened, and the load on the patient can be reduced.

Particularly in a case where the lesion area W2 in the mucous membrane W11 is resected, it may be difficult to recognize a boundary between the lesion area W2 and the normal mucous membrane W11 in some cases. However, since a wide area including the lesion area W2 can be lifted by a plurality of anchoring tools 125, the lesion area can be reliably resected. In a case where physiological salt solution and the like is injected between the mucous membrane W11 and the muscularis W12 by local injection to project the mucous membrane W11 to the inside of the hollow organ W1, the projected mucous membrane W11 may become loose during the resection of the mucous membrane W11. However, in this lifting method using the anchoring tools 125, the mucous membrane W11 can be lifted stably for a long time. Other effects are the same as those of the first embodiment.

Sixth Embodiment

Figure 34:
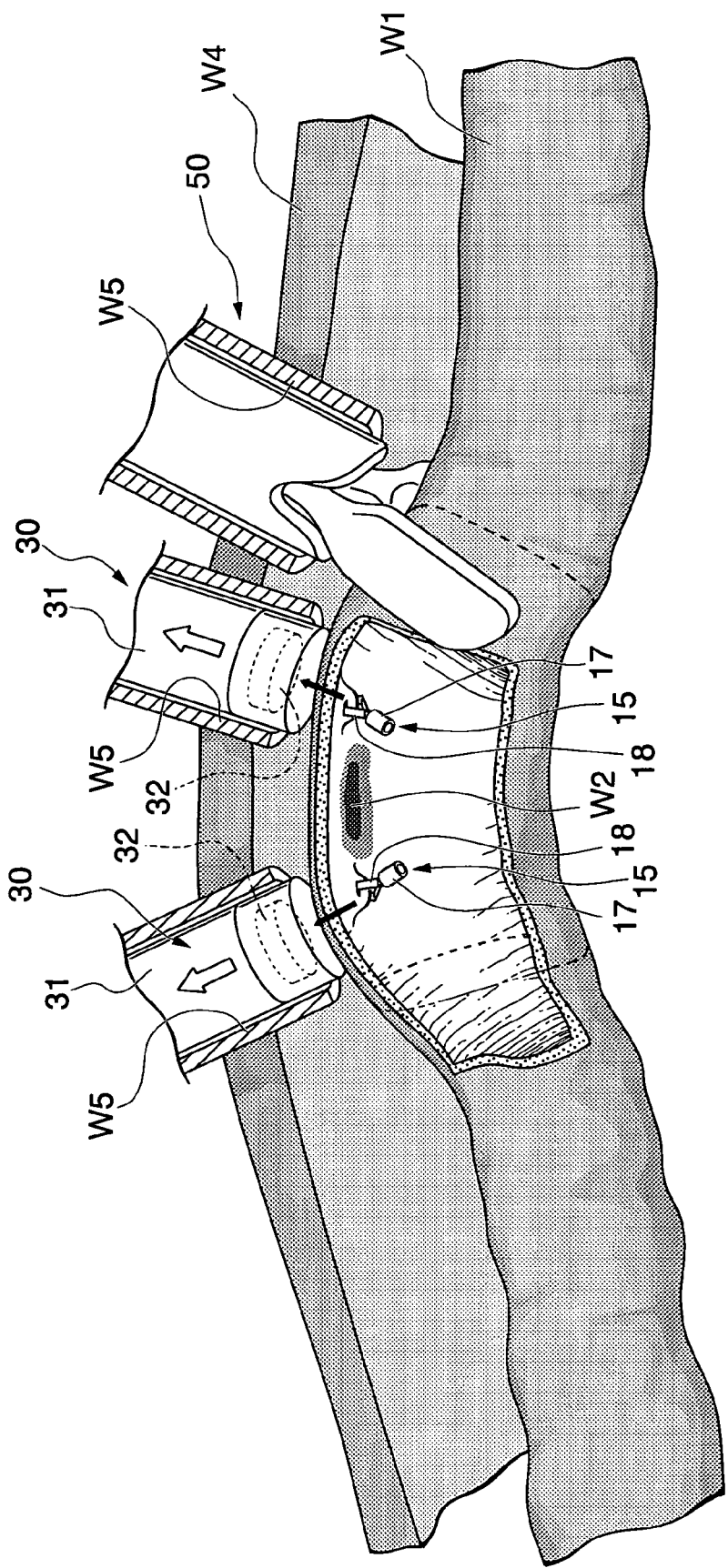
FIG. 34 shows a tissue lifted by two magnet forceps.

FIG. 34 shows a lifting method for when the lesion area W2 is large. Two anchoring tools 15 are anchored around the lesion area W2. The anchoring tool 15 may be an anchoring tool from another embodiment. Two forcep ports W5 are provided in the abdominal wall W4 in the vicinity of the anchor positions of the anchoring tools 15. One magnet forcep 30 is inserted into each forcep port W5 one for each. By means of magnetic fields formed by the magnets 32 of the respective magnet forceps 30, the anchoring tools 15 are attracted to the magnet forceps 30 one to each, and the portion including the lesion area W2 in the hollow organ W1 is pulled up toward the abdominal wall W4. A third forcep port W5 is formed in the abdominal wall W4, and the incision forcep 50 is inserted into this forcep port W5. Then, the portion including the lesion area W2 of the hollow organ W1 is resected.

Figure 35:
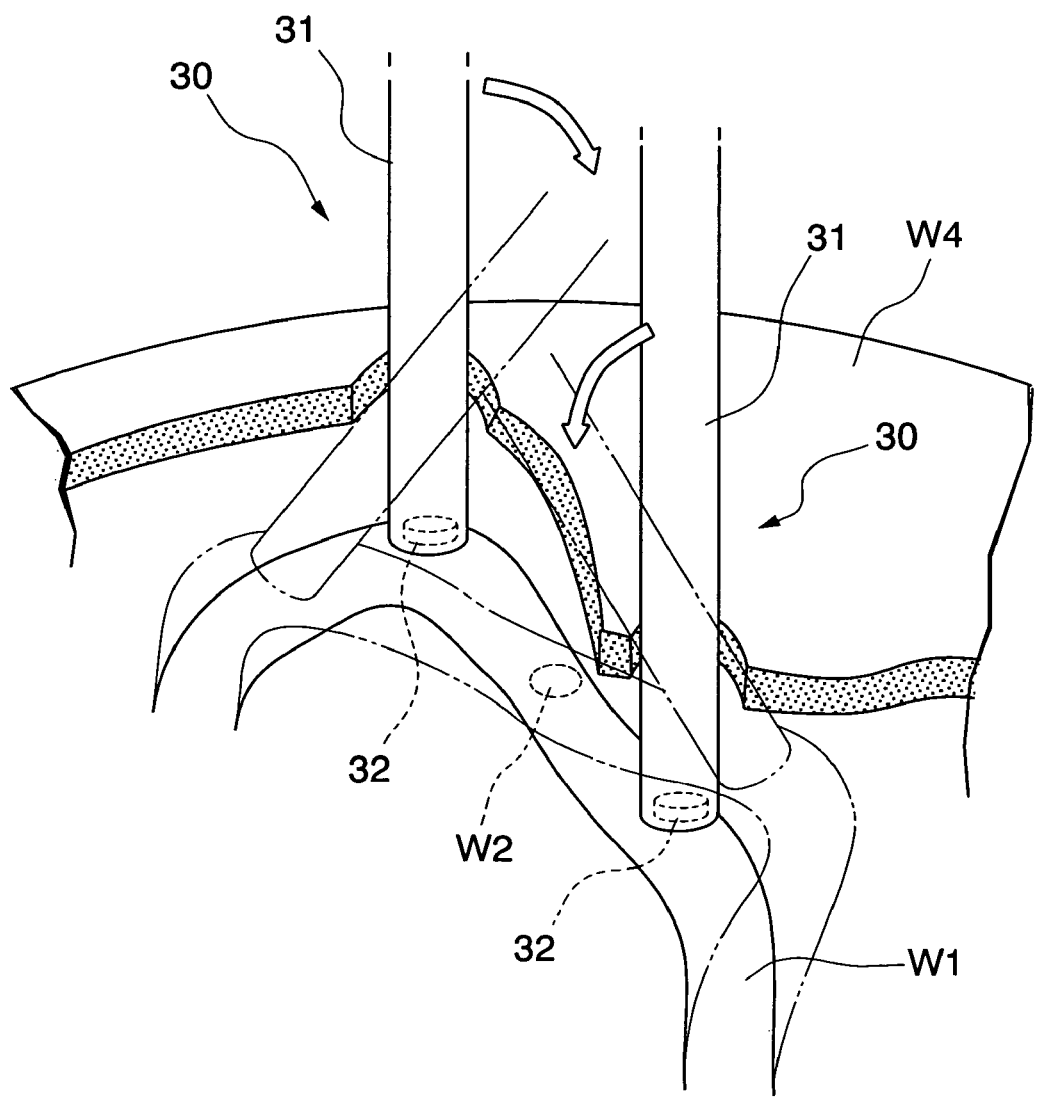
FIG. 35 shows a lifted tissue which is turned by changing directions of the magnet forceps.

At this time, since the lesion area W2 is large, the resection may be difficult from the insertion position of the incision forcep 50, in some cases. As shown in FIG. 35, the two magnet forceps 30 are respectively inclined to the directions shown by the arrows, to perform a turning operation of the hollow organ W1. If the magnet forceps 30 are inclined, the distal ends inserted into the abdominal cavity are moved in the abdominal cavity. Since the anchoring tools 15 attracted to the magnets 32 of the magnet forceps 30 are moved together with the distal ends of the magnet forceps 30, the tissue anchored with the anchoring tools 15 is moved according to this. If the directions in which these two magnet forceps 30 are inclined, are made opposite, then the portion including the lesion area W2 in the hollow organ W1 can be turned.

In the present embodiment, since the position of the lesion area W2 is controlled by changing the orientations of the plurality of magnet forceps 30, the positions of the lesion area W2 and the incision forcep 50 are readily adjusted, facilitating the resection of the tissue including the lesion area W2. If the lesion area W2 is large, the tissue including the lesion area W2 is readily pulled apart from an other organ or tissue. Other effects are the same as those of the first embodiment.

The number of the anchoring tools 15 is not limited to two. The number of the magnet forceps 30 may be three or more. The positional change by the magnet forceps 30 is not limited to turning, and may be variously selected such as inclination and curving. Instead of forming the forcep port W5 to insert the magnet forcep 30, the magnetic field generation tool 140 as shown in FIG. 32 may be used.

Seventh Embodiment

Figure 36:
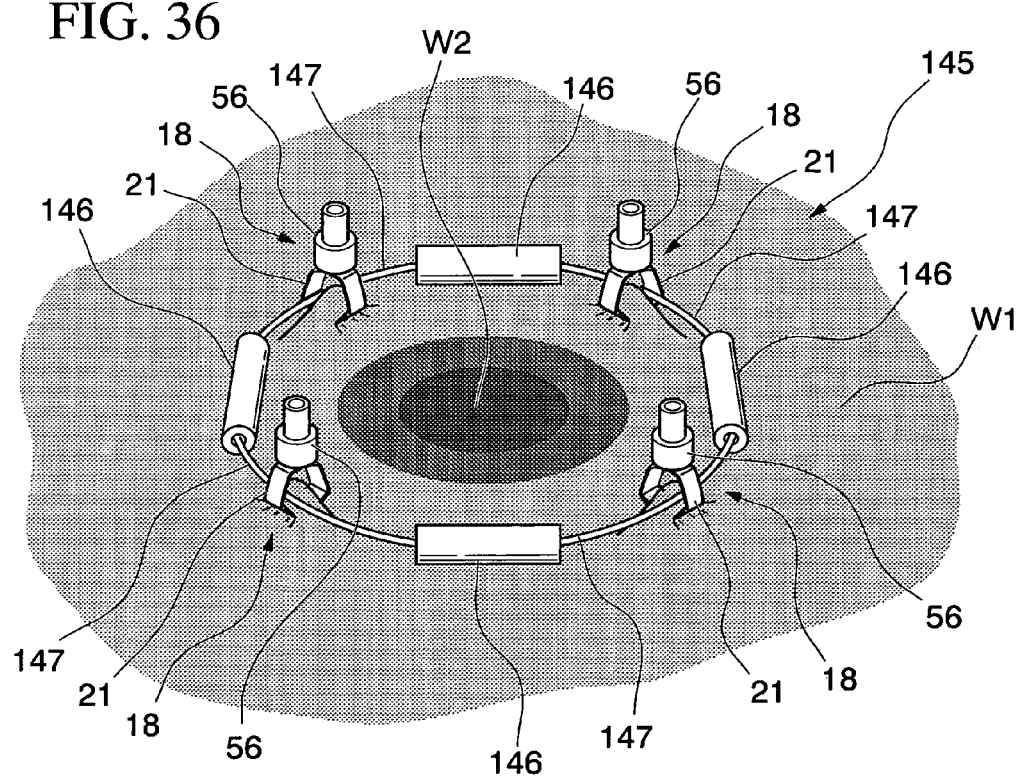
FIG. 36 shows anchored anchoring tools.

FIG. 36 shows anchoring tools of the present embodiment anchored around the lesion area. An anchoring tool 145 has a plurality of clips 18 placed around the lesion area W2, tubes 56 attached to the clips 18, a connection plate 16 (not shown in FIG. 36), a plurality of magnetic bodies 146, and a torus wire 147 sequentially passing through the magnetic bodies 146. For the wire 147, there is used for example, a shape memory wire rod such as a superelastic wire, which spreads in a circular shape in a natural condition, and which retains its shape. The magnetic body 146 has a cylindrical shape formed with a through hole, and the wire 147 is inserted into the through hole. The magnetic body 146 is preferably fixed to the wire 147 so as to avoid positional displacement. However, the magnetic body 146 may be movable along the wire 147.

Figure 37:
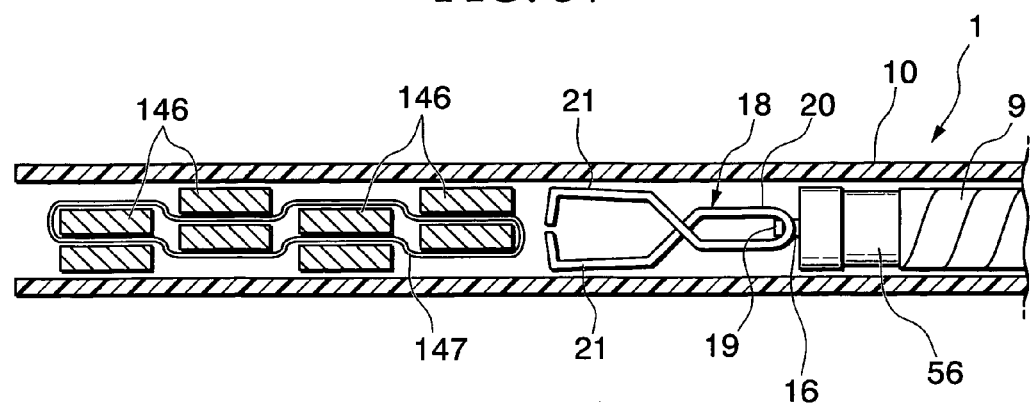
FIG. 37 shows a construction of an anchoring tool and an anchoring device.

As shown in FIG. 37, the magnetic bodies 146 and the wire 147 are contained between the opening of the insertion tube 10 and the distal end of the clip 18 held by the coil sheath 9 of the anchoring device 1. The wire 147 is inserted while the magnetic bodies 146 are flatly bundled, and the plurality of magnetic bodies 146 are aligned approximately in a row in the lengthwise direction of the insertion tube 10. This anchoring device 1 is attached with only one clip 18. The rest of the clips are attached to another anchoring device 1 which does not contain the magnetic bodies 146 and the wire 147. The magnetic body 146 is preferably made from a soft magnetic body so that the respective magnetic bodies 146 are not attracted to each other when the magnetic bodies 146 are contained in the anchoring device 1.

When the anchoring tool 145 is anchored, the anchoring device 1 containing the magnetic bodies 146 and the wire 147 is passed through the working channel 44 of the endoscope 41. By moving the coil sheath 9 forward in the vicinity of the lesion area W2, the magnetic bodies 146 and the wire 147 are pushed out by the clip 18. At this stage, the respective magnetic bodies 146 are not magnetized. Furthermore, since the shape of the wire 147 is memorized, it spreads in an approximate circular shape, and the plurality of magnetic bodies 146 are approximately evenly arranged. After the position is modified so that the lesion area W2 comes to an approximate center of the wire 147, a first clip 18 is placed between any two adjacent magnetic bodies 146. The clip 18 is placed on the tissue while interposing the wire 147 between a pair of arm portions 21. Other anchoring devices 1 are sequentially passed through the working channel 44, and the second and subsequent clips 18 are anchored one by one while interposing the wire 147, in three positions between the magnetic bodies 146.

Figure 38:
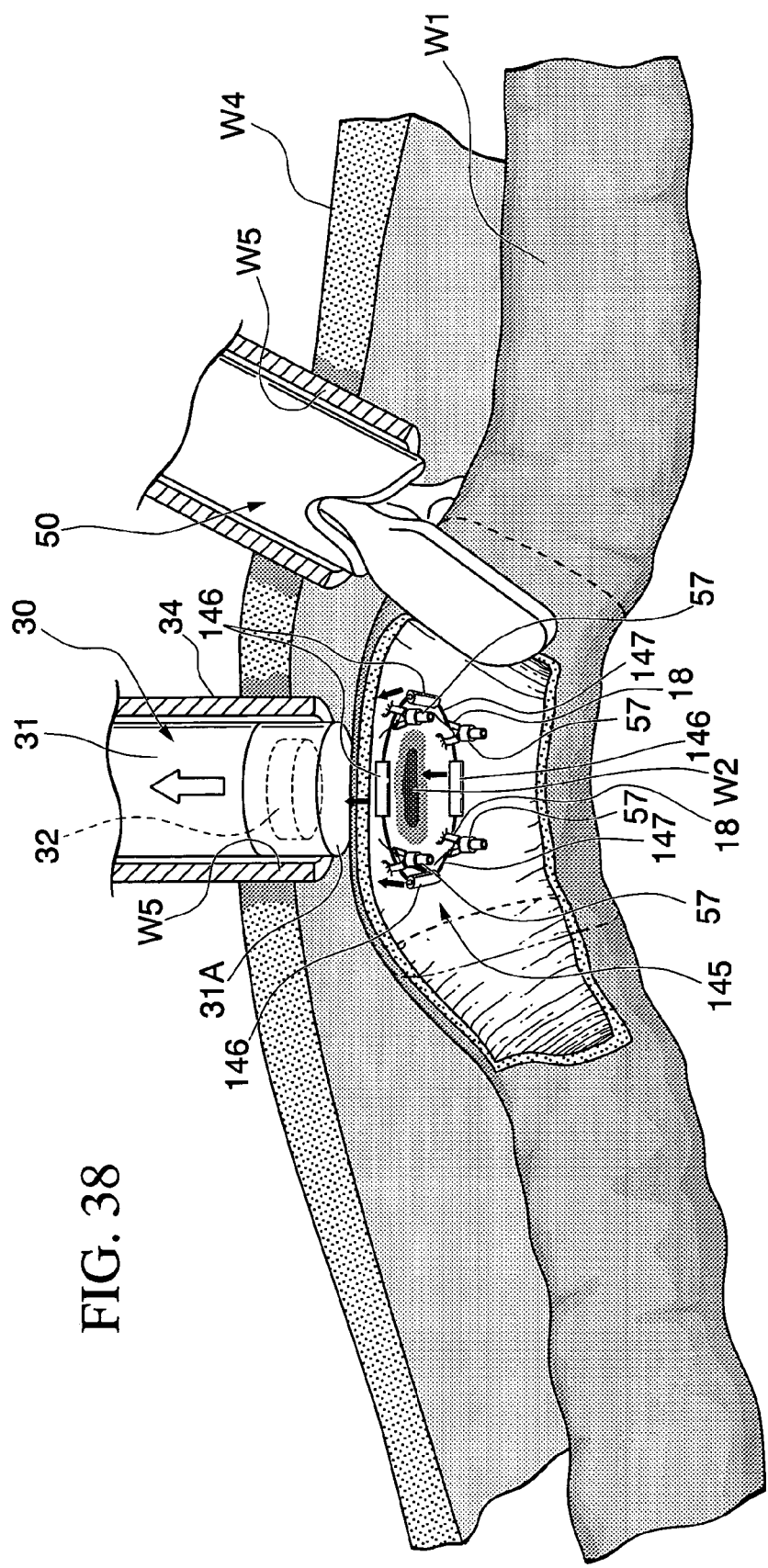
FIG. 38 shows a lifted tissue including a lesion area.

When the tissue including the lesion area W2 is to be lifted, the magnet forcep 30 is brought closer. As shown in FIG. 38, the magnetic bodies 146 are magnetized by the magnetic field of the magnet forcep 30, and attracted to the magnet forcep 30. The tissue is lifted to the magnet forcep 30 side having the area enclosed by the wire 147 as the center. The incision forcep 50 is inserted from the forcep port W5 provided in the abdominal wall W4, and the tissue is resected outside from the area enclosed by the wire 147.

In the present embodiment, since the anchoring tool 145 having a plurality of magnetic bodies 146 linked by the wire 147 is used, the anchoring operation is facilitated. Since the shape of the wire 147 is memorized to be in a circular shape, the plurality of magnetic bodies 146 can be quickly arranged in an approximately circular shape, facilitating the positioning operation for surrounding the lesion area W2. Since the shape of the wire 147 is memorized to be in a circular shape, positional displacement of the magnetic bodies 146 can be prevented, and a predetermined area including the lesion area W2 can be reliably lifted. Other effects are the same as those of the first embodiment.

The length of the wire 147 is preferably a length to allow the lesion area W2 to fit in the area enclosed by the wire 147. However, if the lesion area W2 is large, only a part of the lesion area W2 may be fitted into the area enclosed by the wire 147. Several types of wires 147 having different lengths may be previously prepared and selected according to the size of the lesion area W2.

Eighth Embodiment

Figure 39:
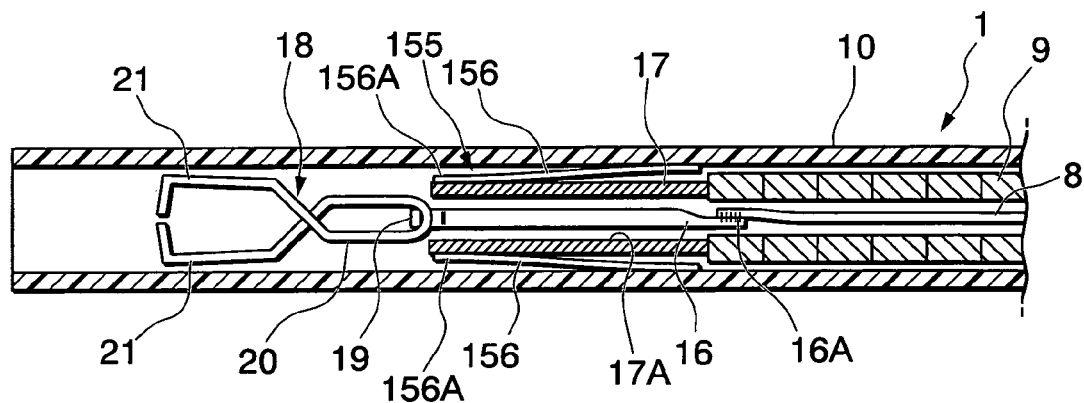
FIG. 39 shows a construction of an anchoring tool and an anchoring device.

FIG. 39 shows an anchoring tool and an anchoring device used in the present embodiment. An anchoring tool 155 has a connection plate 16, a magnetic body tube 17, a clip 18, and laterally extensible plates 156. In the center of the magnetic body tube 17 is formed a hole for passing the connection plate 16 therethrough. The outer circumference on the distal side of the magnetic body tube 17 is fixed with a plurality of, namely four plates 156 at equal intervals. The plates 156 are formed so as to open outwards about a fixation portion 156A on the distal side. When the anchoring tool 155 is contained in the insertion tube 10, the plates 156 are closed by being pushed by the inner circumference of the insertion tube 10.

Figure 40:
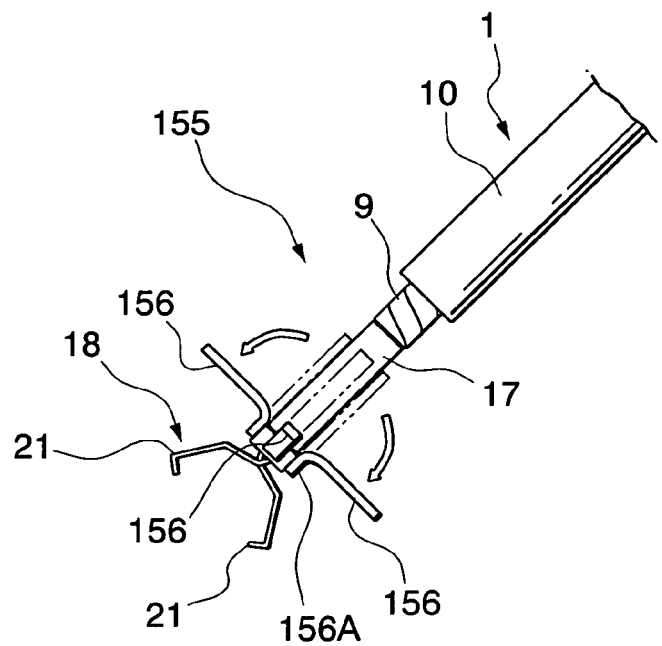
FIG. 40 shows the anchoring tool pushed out, and the plates opened.
Figure 41:
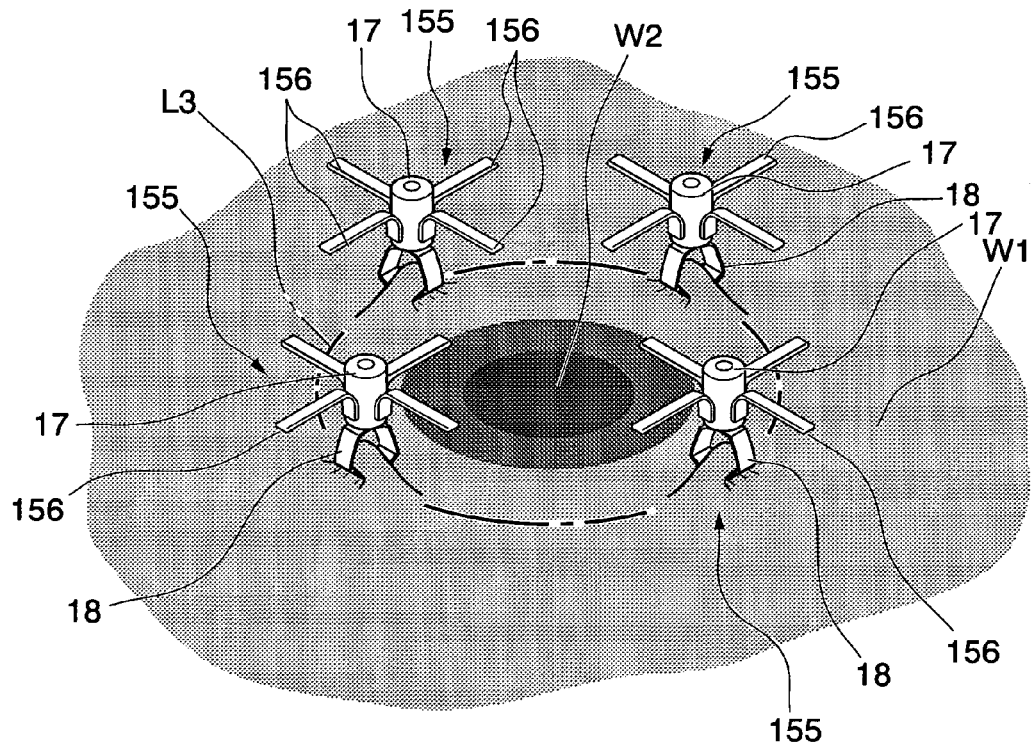
FIG. 41 shows four anchoring tools positioned using the plates, and anchored.

When the anchoring tool 155 is to be anchored, the anchoring device 1 is inserted through the working channel 44 of the endoscope 41 to the periphery of the lesion area W2. When the coil sheath 9 is moved forward with respect to the insertion tube 10, the anchoring tool 155 is pushed out from the insertion tube 10. As shown in FIG. 40, the plates 156 are radially opened about the fixation portion 156A, with the magnetic body tube 17 and the clip 18 as the center. The slider 5 of the operation portion 2 is pulled to open the clip 18, and the clip 18 is pushed onto the tissue in the anchor position. At this time, the clip 18 is pushed onto the tissue so as to overlap the ends of the plates 156 over a visually confirmed boundary between the lesion area W2 and the normal tissue. When the slider 5 is pulled to close the clip 18, the arm portions 21 are latched, thus clamping the tissue. When the welded portion between the wire 8 and the connection plate 16 is broken, the anchoring tool 155 is anchored. Once the first anchoring tool 155 has been anchored, the operation up to here is repeated. As shown in FIG. 41, the second and subsequent anchoring tools 155 are anchored as shown by the imaginary line L3, respectively in positions separated from the outer edge of the lesion area W2 by the length of the plates 156, so that the lesion area W2 is surrounded by four anchoring tools 155.

Figure 42:
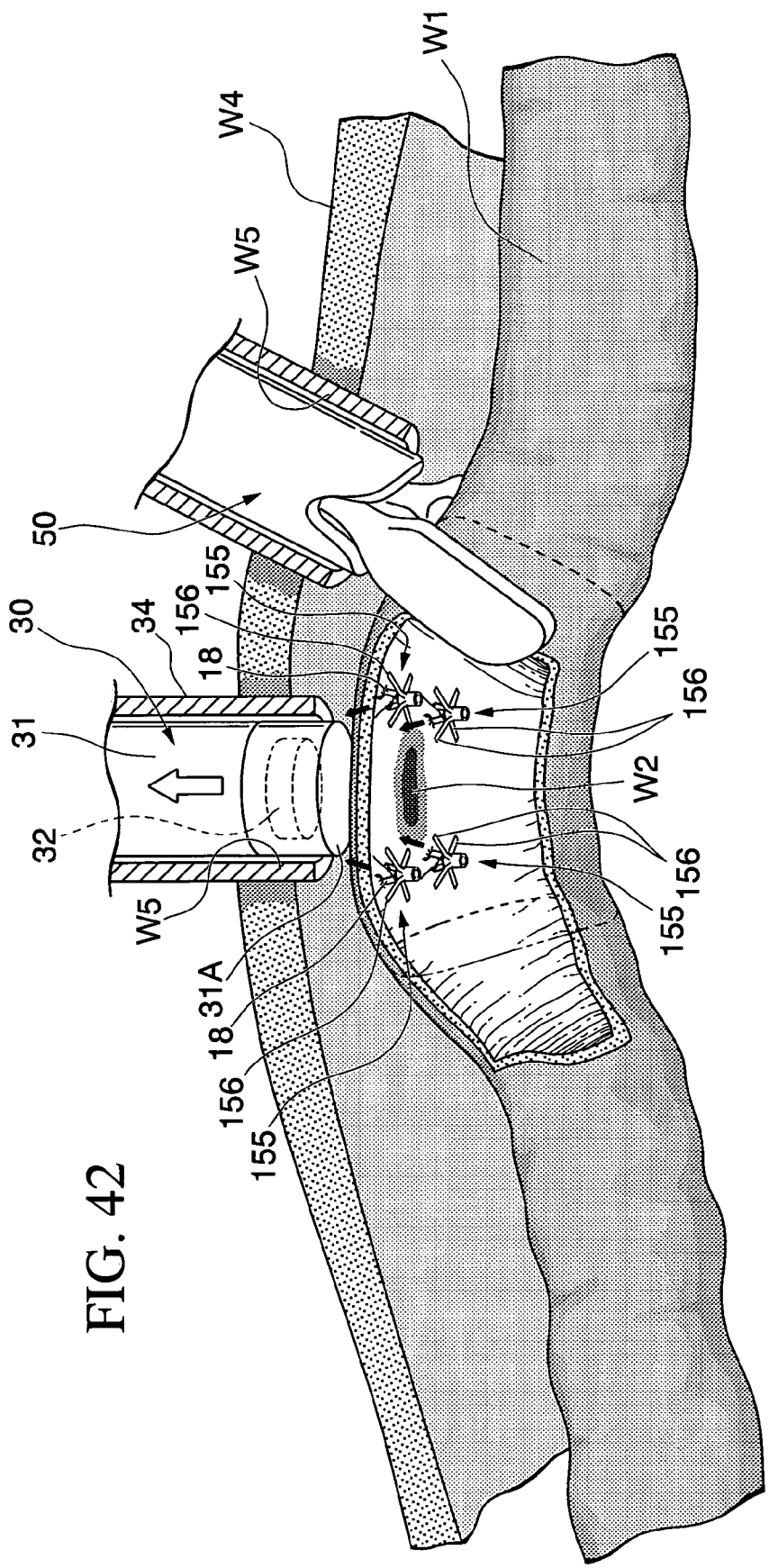
FIG. 42 shows a lifted tissue including a lesion area.

When the tissue including the lesion area W2 is lifted, the magnet forcep 30 is brought closer. As shown in FIG. 42, by means of the magnetic field of the magnet forcep 30, the magnetic body tubes 17 are attracted to the magnet forcep 30, and the tissue including the lesion area W2 is lifted to the magnet forcep 30 side. The incision forcep 50 is then inserted from the forcep port W5, and the tissue is resected further outside than the area surrounded by the anchoring tools 155.

The length of the plate 156 serves as a guide for a margin from the lesion area W2 to the resection position, by visual observation. An appropriate value of such a margin differs depending on the type of lesion, and the resection method. Therefore, preferably, a plurality of anchoring tools 155 having different lengths of plates 156 are previously prepared, and an anchoring tool 155 having an appropriate length of plates 156 is selected. The number of the plates 156 is not limited to four. It may be one to three, or it may be four or more.

According to the present embodiment, it becomes possible to place the clips 18 so as to border positions which are outside by the length of the plate 156 from the visually observed lesion area W2, thus facilitating the positioning. It is possible that the tissue around the visually observed lesion area W2 looks normal if only observed by the naked eye, but actually contains cancer at a cellular level in the vicinity of the boundary. Moreover, if the tissue is resected using an electric scalpel, the tissue is burned. Therefore diagnosis of the specimen as to whether or not the tissue of the burned portion is normal or lesion is not possible. In the present embodiment, since it is resected with an appropriate margin using the length of the plate 156, a situation where lesions are left behind can be prevented. Other effects are the same as those of the first embodiment.

The plates 156 may be fixed to the clip 18. Moreover plates 156 having different lengths may be fixed around the circumferential direction. Positioning can be performed using plates 156 of an appropriate length for the lesion area W2. In the case where the lengths of the plates 156 are made different according to the location, confirmation can be readily performed by visual observation if colors are changed for each plate 156.

The present invention can be widely applied without being limited by the respective embodiments mentioned above.

For example, the plates 156 may be fixed to an anchoring tool of another embodiment. The plates 156 may be fixed to the clip 18. Another channel may be attached to the endoscope 41, and an anchoring tool (such as the anchoring tool 15) may be inserted through this channel.

Moreover, the working channel 44 need not be integrally provided in the endoscope 41. In this case, for example, while observing by a swallowable observation device such as a capsule endoscope, a working channel having no observation function (it may have an observation function, however without the observation function, the diameter can be reduced and the load on the patient can be further reduced) may be introduced into the body so as to perform the treatment as mentioned above.

What is claimed is:

1. A lifting method for a lesion area, comprising:
    a step of introducing at least three anchoring tools, each having its own separate soft magnetic body and an anchor into a hollow organ having a lesion area, by using a working channel inserted from a natural opening into the hollow organ;
    a step of anchoring the at least three anchoring tools, by sequentially placing the at least three anchoring tools in predetermined positions outside of the lesion area to define a border between a normal tissue area and the lesion area so as to arrange a plurality of the soft magnetic bodies which are not attracted to each other around the lesion area in a state that the plurality of the soft magnetic bodies are unmagnetized;
    a step of creating at least three lifting points using the at least three anchoring tools around the lesion area including the normal tissue; and
    a step of lifting portions including the border between the normal tissue area and the lesion area and being around the at least three lifting points in a substantially vertical direction with respect to the lesion area by magnetizing the at least three soft magnetic bodies using a magnetic field generation tool arranged on the outside of the hollow organ so that the at least three anchoring tools are attracted to the magnetic field generation tool.

2. The lifting method for a lesion area according to claim 1, wherein the step of lifting comprises lifting the tissue including the entirety of the lesion area toward an abdominal wall of a living body.

3. The lifting method for a lesion area according to claim 2, wherein the step of lifting comprises a step of inserting a magnet serving as the magnetic field generation tool, percutaneously from the outside of the hollow organ.

4. The lifting method for a lesion area according to claim 1, wherein the step of anchoring the anchoring tools comprises a step of placing the anchor so that the soft magnetic body does not move from the anchor position.

5. The lifting method for a lesion area according to claim 2, comprising a step of inserting a plurality of magnets, percutaneously to the outside of the hollow organ.

6. The lifting method for a lesion area according to claim 5, comprising a step of changing a posture of the lifted tissue by moving the magnets.

7. The lifting method for a lesion area according to claim 1, wherein the step of introducing the anchoring tools into the hollow organ comprises a step of inserting an endoscope comprising the working channel and an observation device into the hollow organ, and introducing the anchoring tools through the working channel.

8. The lifting method for a lesion area according to claim 1, comprising a step of lifting the lesion area from an opposite side to the side having the anchors placed, to the inside of the hollow organ, using the magnetic field generation tool.

9. The lifting method for a lesion area according to claim 1, wherein the step of lifting comprises lifting the border including the entirety of the lesion area towards the outside of the hollow organ.

10. The lifting method for a lesion area according to claim 9, further comprising a step of cutting out the entirety of lesion area and the portions of tissue outside of the lesion area from the outside of the hollow organ.

\* \* \* \* \*